United States Patent [19]

Doherty et al.

[11] Patent Number: 5,149,692
[45] Date of Patent: Sep. 22, 1992

[54] BISALKOXYPHOSPHINYL COMPOUNDS AS RENIN INHIBITORS

[75] Inventors: Annette M. Doherty, Ann Arbor; Harriet W. Hamilton; Bruce A. Steinbaugh, both of Chelsa, all of Mich.

[73] Assignee: Warner-Lambert Company, Morris Plains, N.J.

[21] Appl. No.: 454,795

[22] Filed: Dec. 21, 1989

[51] Int. Cl.$^5$ .............................. C07K 5/06; C07K 5/08
[52] U.S. Cl. ........................................ 514/18; 514/19; 530/331; 548/344; 548/496; 562/444; 562/445; 562/559; 562/575
[58] Field of Search ................ 530/331; 514/18, 19; 562/444, 575, 445, 559; 548/344, 496

[56] References Cited

U.S. PATENT DOCUMENTS 4,845,079  7/1989  Luly et al. .

FOREIGN PATENT DOCUMENTS 0184855  6/1986  European Pat. Off. .
0192554  6/1986  European Pat. Off. .
0209848  1/1987  European Pat. Off. .
0210545  2/1987  European Pat. Off. .
0220665  6/1987  European Pat. Off. .
2212804  11/1988  United Kingdom .

OTHER PUBLICATIONS

ASM News, vol. 56, No. 7 (Jul. 1990), "HIV Protease Inhibitors," p. 368.
Burger, Alfred, ed. "Medicinal Chemistry", 2nd ed. pp. 565-571, 578-581, 600-601 (1960).
Bolis et al., "Renin Inhibitors, Dipeptide Analogues of . . . " J. Med. Chem. 1987, 30, 17 29-1737.
Dehke Walker et al., Progress in Drug Research, vol. 10 pp. 510-512 (1967).
Haber et al. "Renin Inhibitors: A Search for Principles of Design," J. Cardovascular Pharm. 10 (Supp. 7): 554-558 (1987).
Plattner et al. "Renin Inhibitors, Dipeptide Analogues of . . . " J. Med. Chem. (1981) 31, 2277-2288.
Journal of Hypertension 1990, 8:251-259, L. W. Schaffer et al., "Acute Hypotensive responses to peptide . . . ".
Drugs, 35:495-503 (1988), F. R. Buhler, "Antihypertensive Treatment According to Age, Plasma Renin and Race".
Handbook of Hypertension, v. 5:272-311, C. I. Johnston, "Angiotensin Converting Enzyme Inhibitors".
Clinical and Experimental Pharmacology & Physiology, (1982) Suppl. 7,63-71, J. R. Knill, "Development of Captopril . . . ".
American Journal of Cardiology, v. 66:2D-6D, J. N. Cohn, "Mechanisms in Heart Failure and the Role of Angiotensin . . . ".
New England Journal of Medicine, Jan. 11, 1990, 100-110, A. M. Katz, "Cardiomyopathy of Overload".
Circulation, v.80, No. 3, Sep. 1989, pp. 693-699, S. H. Rahimtoola, "The Pharmacologic Treatment . . . ".
American Journal of Cardiology, Jan. 1, 1991, 63-66, G. N. Neuberg et al., "Hemodynamic Effects of Renin . . . ".

Primary Examiner—Howard E. Schain
Attorney, Agent, or Firm—Elizabeth M. Anderson

[57] ABSTRACT

The invention concerns novel renin-inhibitory peptides which are useful for treating renin-associated hypertension, congestive heart failure, hyperaldosteronism, glaucoma, and diseases caused by retroviruses including HTLV-I, -II, -III. Processes for preparing the peptides, novel intermediates useful in the preparation thereof, compositions containing them, and methods of using them are included. Also included is a diagnostic method which uses the compounds to determine the presence of renin-associated hypertension, congestive heart failure, or hyperaldosteronism.

17 Claims, No Drawings

BISALKOXYPHOSPHINYL COMPOUNDS AS RENIN INHIBITORS

BACKGROUND OF THE INVENTION

Renin is a natural enzyme which is released into the blood from the kidney. It cleaves its natural substrate, angiotensinogen, releasing decapeptide, angiotensin I. This is in turn cleaved by converting enzyme in the lung, kidney and other tissues to an octapeptide, angiotensin II. Angiotensin II raises blood pressure both directly by causing arteriolar constriction and indirectly by stimulating release of the sodium-retaining hormone aldosterone from the adrena gland causing a rise in extracellular fluid volume. Inhibitors of renins have been sought as an agent for control of hypertension, congestive heart failure, and hyperaldosteronism.

The present invention concerns novel peptides which inhibit renin. It also concerns pharmaceutical compositions containing these novel peptides, methods of treating renin-associated hypertension, congestive heart failure, glaucoma, and hyperaldosteronism, as well as the use of the peptides as diagnostic tools, and the methods for preparing the peptides.

Since HIV protease, like renin, is an aspartyl protease, the compounds of the instant invention can also be used to treat diseases caused by retroviruses including HTLV-I, -II, and -III.

European Application No. 184,855 covers renin-inhibitory peptides of the formula $$A-N\underset{R_2}{\overset{}{|}}-CH(R_1)-\underset{O}{\overset{O}{\|}}C-N\underset{R_2}{\overset{R_3}{|}}-CH(R_3)-\underset{O}{\overset{O}{\|}}C-N\underset{R_5}{\overset{R_4}{|}}-CH-\overset{OH}{\overset{|}{C}}H-CH(R_6)-\underset{R_9}{\overset{O}{\|}}C-N-X$$

wherein A is an N-protecting group; $R_1$, $R_3$, $R_5$ and $R_7$ are lower alkyl or lipophilic or aromatic amino acid side chains and may be the same or different; $R_2$, $R_4$ and $R_6$ are hydrogen or lower alkyl and may be the same or different; X is hydrogen, lower alkyl or $-CH_2-OR_8$, wherein $R_8$ is hydrogen, lower alkyl or alkaryl; and $R_9$ is lower alkyl, hydroxy, hydroxyalkyl, alkoxy, allyl, alkaryloxy or thioalkyl and pharmaceutically acceptable salts thereof.

European Application No. 192,544 covers peptide pepstatin analogues of the formula $$R_1NH-CH(R_2)-CONH-CH(R_3)-CONH-CH(CH_2Z_1)-CHOH-CH_2-CO-X-Y-R_4$$

wherein $R_1$ is COR or $SO_2R^1$; $R_2$ is optionally substituted lower alkyl, phenyl, naphthyl, cyclohexyl or pyridyl; $R_3$ is hydrogen, lower alkenyl, phenyl, naphthyl, 3-6C cycloalkyl, monocyclic heterocyclic or substituted lower alkyl; $Z_1$ is i-Pr, phenyl, cyclohexyl; X-Y is a dipeptide.

European Application No. 220,665 covers peptidyl, amino cycloalkyl, hydroxy alkanoic acid derivatives of the formula $$X-Z-NR_2-CHR_3-CHOH-(CHR_4)_n-CO-E$$

wherein $X = H$, $R_1OC_mH_{2m}CO$, $R_1C_mH_{2m}OCO$, $R_1C_mH_{2m}CO$, $R_1SO_2$, $Q-C_rH_{2r}CO$, $H(NHCH_2CH_2)_mNHCH_2CO$ or 9-fluorenyl—$C_mH_{2m}OCO$;

$Z = 1-4$ peptide-linked aminoacid groups selected from Abu, Ada, Ala, Arg, Asn, Bia, Cal, Dab, Gln, Gly, His, N(im)-alkyl-His, Ile, Leu, tert-Leu, Lys, Met, α-Nal, β-Nal, Nbg, Nle, Orn, Phe, Pro, Ser, Thr, Tic, Trp, Tyr and Val; and $E = OH$, OA, $NH_2$, NHA or $N(A)_2$.

The compounds are useful as renin and acid protease inhibitors.

European Application 209,848 covers phosphorous-containing amino acids as inhibitors of renin and angiotensin converting enzyme of the formula $$A-B-D-E-G$$

wherein

A is, e.g., benzyloxycarbonyl, t-butoxycarbonyl, 1-naphthyloxyacetyl or 1-naphthylacetyl;

B is, e.g., phenylalanine, 3-(1-naphthyl)alanine), tryptophan or homophenylalanine;

D is, e.g., histidine, lysine or phenylalanine;

E is, e.g., one of the following formulae:

$$NH_2-CH(CH_2-C_6H_{11})-P(=O)(OCH_3)-CH_2-CH(CH_2CH(CH_3)_2)-CO_2H$$

or $$NH_2-CH(CH_2-C_6H_{11})-P(=O)(OH)-CH_2CH_2-CH(CH_3)_2$$

and G is e.g., —OH, —OEt, —$NH_2$. Those compounds inhibit enzymes and can be used as pharmaceutical agents.

European Application 210,545 covers phosphorous-containing amino acids and dipeptide compounds of the formula $$A-E-G$$

wherein

A is, e.g., hydrogen, or $R_1-$, $R_bCO$ or $R_bSO_2-$ where $R_a$ and $R_b$ are e.g., alkyl, cycloalkyl, or aryl;

E is

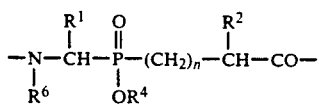

G is —R³ or is

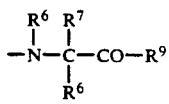

wherein
R¹ is, e.g., alkyl;
n is 0,1;
R² is, e.g., hydrogen or alkyl;
R³ is OH, NH₂, NHR$_{a'}^3$, NR$_{a'}^3$N$_{b'}^3$,
OR$_a^3$ where R$_{b'}^3$, and R$_c^3$ are e.g., alkyl;
R⁴ is, e.g., hydrogen or alkyl;
R⁶ is H or methyl;
R⁷ is, e.g., hydrogen or alkyl;
R⁸ is, e.g., hydrogen, methyl or cycloalkyl such that when R⁹ is cycloalkyl, R⁶ and R⁷ are hydrogen;
R⁹ is, e.g., hydroxy.

The compounds have enzyme inhibitor activity, e.g., renin inhibition or angiotensin converting enzyme inhibition.

U.S. Pat. No. 4,845,079 covers peptidylaminodiols of the formula

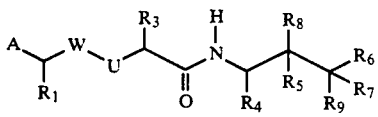

wherein A is a substituent; W is C=O or CHOH; U is CH₂ or NR₂, provided when W is CHOH then U is CH₂; R₁ is loweralkyl, cycloalkylmethyl, benzyl, 4-methoxybenzyl, halobenzyl, (1-naphthyl)methyl, (2-naphthyl)methyl, (4-imidazoly)methyl, α,α-dimethylbenzyl, 1-benzyloxyethyl, phenethyl, phenoxy, thiophenoxy or anilino; R₂ is hydrogen or loweralkyl; R₃ is loweralkyl, [(alkoxy)alkoxy]alkyl, (thioalkoxy)alkyl, loweralkenyl, benzyl or heterocyclic ring substituted methyl; R₄ is loweralkyl, cycloalky-methyl or benzyl; R₅ is vinyl, formyl, hydroxymethyl or hydrogen; R₇ is hydrogen or loweralkyl; R₈ and R₉ are independently selected from OH and NH₂; and R₆ is hydrogen, loweralkyl, vinyl or arylalkyl; provided that when R₅ and R₇ are both hydrogen and R₈ and R₉ are OH, the carbon bearing R₅ is of the "R" configuration and the carbon bearing R₆ is of the "S" configuration; or pharmaceutically acceptable salts or esters thereof as renin inhibitors for the treatment of hypertension.

British Patent Application 2,212,804 covers N-heterocyclic alcohol derivatives of the formula

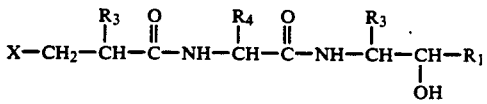

are disclosed. These compounds are inhibitors of renin and therefore useful as cardiovascular agents.

The symbols have the following definitions:

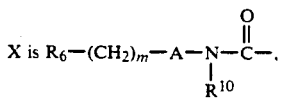

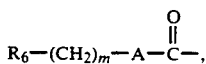

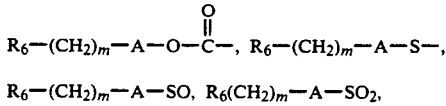

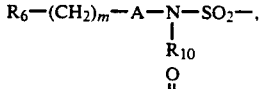

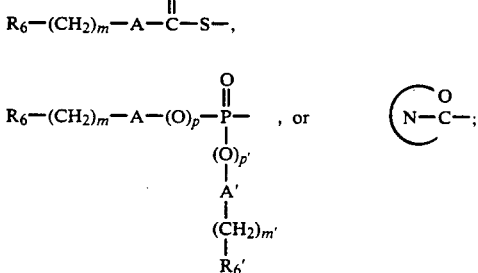

R₁ is fully saturated, partially saturated, or unsaturated monocyclic N-heterocyclic ring of five or six atoms containing at least one N atom or a bicyclic ring in which said N-heterocyclic ring is fused to a benzene ring.

R₃, R₄, and R₆ are independently selected from hydrogen or optionally substituted alkyl, m, m', and m" are zero or an integer from 1 to 5;
n is an integer from one to five;
p and p' are zero or 1;
g is an integer from 2 to 5;
R₁₀ is —(CH₂)$_m$—R₆';
A and A' are a single bond or —(CH)—(CH₂)$_m$—R₆",
and R₆, R₆', and R₆" are independently selected from hydrogen, alkyl, and aryl, and cycloalkyl, or R₆ and R₆' taken together with the atom to which they are bonded may form a ring of three to five carbons.

SUMMARY OF THE INVENTION

The present invention relates to novel peptides of the formula

A—X—Y—W—U   (I)

and the pharmaceutically acceptable acid addition salts thereof wherein A, X, Y, W, and U are as defined herein below.

The invention also includes pharmaceutical compositions comprising an effective amount of the above peptide of formula I in admixture with a pharmaceutically acceptable carrier or excipient, and a method for treating renin-associated hypertension in a patient suffering therefrom comprising administering to said patient the above pharmaceutical composition in unit dosage form.

Further the invention includes a pharmaceutical composition comprising an effective amount of a peptide of formula I above in admixture with a pharmaceutically acceptable carrier or excipient, and a method for treating hyperaldosteronism in a patient suffering therefrom comprising administering to said patient the above pharmaceutical composition in unit dosage form.

Further the invention includes a pharmaceutical composition comprising an effective amount of a peptide of formula I in admixture with a pharmaceutically acceptable carrier or excipient, and a method for treating congestive heart failure in a patient suffering therefrom comprising administering to said patient the above pharmaceutical composition in unit dosage form.

Further, the invention includes a pharmaceutical composition comprising an amount effective for treating retroviruses of a peptide of formula I in admixture with a pharmaceutically acceptable carrier or excipient, and a method of treating diseases caused by retroviruses in a patient suffering therefrom comprising administering to said patient the above composition in unit dosage form.

The present invention also includes the use of peptides of formula I above as diagnostic tools for the identification of cases of hypertension due to renin excess.

The invention further includes methods for preparing peptides of formula above and novel intermediates used in their preparation.

DETAILED DESCRIPTION

The following table provides a dictionary of the terms used in the description of the invention.

TABLE 1

| Abbreviated Designation | Amino Acid |
|---|---|
| LEU | L-Leucine |
| HIS | L-Histidine |
| TZA | 2(S)-Amino-3-(4-thiazolyl)-propanoic acid (4-Thiazolylalanine) |
| STA | 4(S)-Amino-3(S)-hydroxy-6-methylheptanoic acid |
| PHSTA | 4(S)-Amino-3-(S)-hydroxy-5-phenylpentanoic acid |
| CYSTA | 4(S)-Amino-3-(S)-hydroxy-5-cyclohexanepentanoic acid |
| ILE | L-Isoleucine |
| PHE | L-Phenylalanine |
| PHE(OBn) | L-Phenylalanine benzyl ester |
| HOMOPHE | 2(S)-Amino-5-phenylpentanoic acid (Homophenylalanine) |
| GLY | Glycine |
| LYS | L-Lysine |
| MET | L-Methionine |
| MET(O) | L-Methionine-sulfoxide |
| MET(O$_2$) | L-Methionine-sulfone |
| NAPHTHYLALA | 2(S)-Amino-3-(1-naphthyl)-propanoic acid (1-Naphthylalanine) |
| CYCLOHEXYLALA | Cyclohexylalanine (Hexahydro-L-phenylalanine) |
| TYR | L-Tyrosine |
| TYR(OMe) | O-Methyl-L-tyrosine |
| TRP | L-Tryptophan |
| GLN | L-Glutamine |
| (NMe)PHE | N-Methyl-L-phenylalanine |
| ASTA | 3(RS), 4(S)-Diamino-6-methylheptanoic acid |
| ACYS | 3(RS), 4(S)-Diamino-5-cyclohexanepentanoic acid |
| DFKSTA | 4(S)-Amino-3-oxo-2,2-difluoro-6-methylheptanoic acid |
| DFSTA | 4(S)-Amino-3(R)-hydroxy-2,2-difluoro-6-methylheptanoic acid |
| DFKCYS | 4(S)-Amino-3-oxo-2,2-difluoro-5-cyclohexane pentanoic acid |
| DFCYS | 4(S)-Amino-3(R)-hydroxy-2,2-difluoro-5-cyclohexane pentanoic acid |
| DFKCHS | 4(S)-Amino-3-oxo-2,2-difluoro-4-cyclohexane butanoic acid |
| DFCHS | 4(S)-Amino-3(R)-hydroxy-2,2-difluoro-4-cyclohexane butanoic acid |
| ALG | 2(S)-Amino-4-pentenoic acid (Allylglycine) |
| CAD | 2(S)-Amino-1-cyclohexyl-6-methyl-3-(R),4(S)-heptanediol |
| CDH | 2(S)-Amino-1-cyclohexyl-3,5-heptanediol |
| PGY | 2(S)-Aminopentanoic acid (Propylglycine) |
| PPG | 2(S)-Amino-4-pentynoic acid (Propargylglycine) |
| CPM | 2(S)-Amino-3-cyclopropane-propanoic acid (Cyclopropylalanine) |
| EMG | 2(S)-Amino-4,5(RS)-epoxy-4-pentenoic acid |
| BYG | 2(S)-Aminohexanoic acid (Butylglycine) |
| NIA | 2(S)-Amino-3-cyanopropanoic acid (cyanoalanine) |
| PHA | 2(S)-Amino-6-(1-pyrrolo)hexanoic acid |
| ATM | 2(S)-Amino-3-(2-amino-5-thiazole)propanoic acid |

Amides With

| | |
|---|---|
| —NHCH$_2$CH$_2$-(pyridine) | 2-Aminoethylpyridine |
| —NHCH$_2$CH$_2$—N(morpholine)O | 2-Aminoethylmorpholine |
| —NH—CH$_2$-(pyridine) | 2-Aminomethylpyridine |
| —NHCH$_2$CHCH$_2$CH$_3$ \| CH$_3$ | 2-Methylbutylamine |
| —NHCH$_2$CH$_2$N(CH$_2$CH$_2$OH)$_2$ | 2-(Bis(2-Hydroxyethyl)amino)-ethylamine |
| —N(ring)O | Morpholine |

| Abbreviated Designation | Protecting Group |
|---|---|
| Z | Benzyloxycarbonyl |
| BOC | Tert-butyloxycarbonyl |
| TR | Triphenylmethyl |
| TBS | t-Butyldimethylsilyl |
| TROC | 2,2,2-Trichloroethyl oxycarbonyl |
| THP | Tetrahydropyran |

Esters With

| | |
|---|---|
| —OCH$_3$ | Methanol |
| —OC$_2$H$_5$ | Ethanol |
| —OCH(CH$_3$)$_2$ | 2-Propanol |
| —OC(CH$_3$)$_3$ | tert-Butanol |
| —OBZL | Benzyl alcohol |

Solvents and Reagents

| | |
|---|---|
| DMF | N,N-Dimethylformamide |
| DMSO | Dimethylsulfoxide |
| HOBT | Hydroxybenzotriazole |

TABLE 1-continued

| | |
|---|---|
| DCC | N,N'-Dicylohexylcarbodiimide |
| HOAc | Acetic acid |
| Et₃N | Triethylamine |
| THF | Tetrahydrofuran |
| CH₂Cl₂ | Dichloromethane |

The peptides of the present invention are represented by the formula $$A-X-Y-W-U \qquad I$$

and the pharmaceutically acceptable acid addition salts thereof, wherein A is

X is PHE, HOMOPHE, TYR, TYR(OMe), NAPHTHYLALA, CYCLOHEXYLALA, LEU, TRP, HIS, or (NMe)PHE;
Y is GLN, HIS, LEU, PGY, MET, MET(O), MET(O₂), TZA, ALG, PPG, CPM, EMG, BYG, NIA, PHA, ATM, GLY,

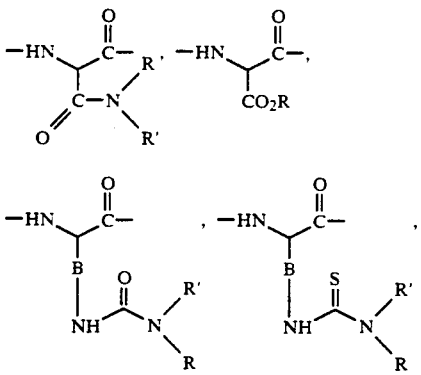

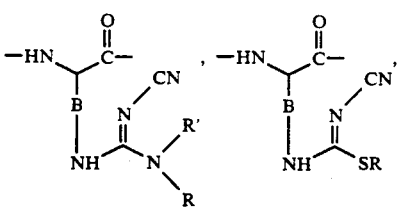

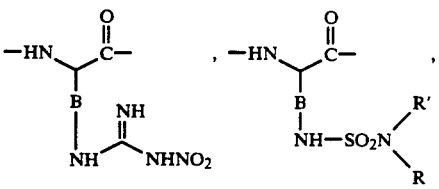

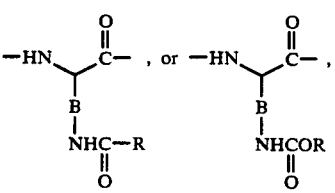

wherein R and R' are each independently H, benzyl, or lower alkyl or lower alkenyl; B is a chain of from three to six carbon atoms which is saturated, olefinic, or acetylenic;

W is STA, CYSTA, or PHSTA, DFSTA, DFKSTA, DFCYS, DFKCYS, DFCHS, DFKCHS, ASTA, or ACYS, CAD, or CDH;

U is hydrogen,

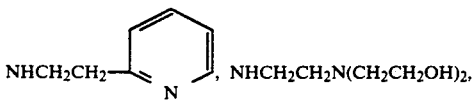

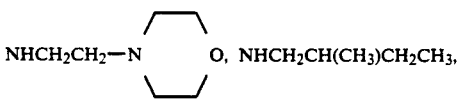

or

Preferred compounds of the present invention are those wherein A is

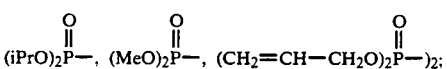

X is PHE, or TYR(OMe); W is STA, DFKCYS, DFCYS, DFSTA, DFKSTA, CAD or CYSTA; U is hydrogen,

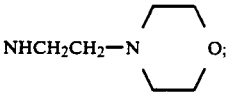

NHCH₂CH₂N(CH₂CH₂OH)₂ or NHCH₂CH(CH₃)CH₂CH₃; and Y is HIS,

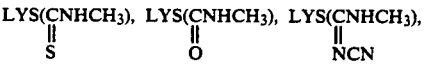

LYS(CNHNO₂), TZA, ALG, ATM, PGY, MET, GLY, PPG NH

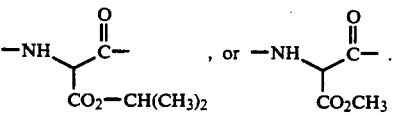

Particularly valuable compounds falling within the scope of the invention include the following:

(iPrO)₂P(=O)—TYR(OMe)—HIS—STA—NHCH₂CH(CH₃)CH₂CH₃,

(MeO)₂P(=O)—TYR(OMe)—HIS—STA—NHCH₂CH(CH₃)CH₂CH₃,

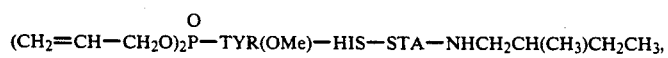
(CH₂=CH—CH₂O)₂P(=O)—TYR(OMe)—HIS—STA—NHCH₂CH(CH₃)CH₂CH₃,

(iPrO)₂P(=O)—PHE—HIS—STA—NHCH₂CH(CH₃)CH₂CH₃,

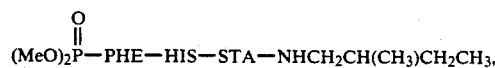
(MeO)₂P(=O)—PHE—HIS—STA—NHCH₂CH(CH₃)CH₂CH₃,

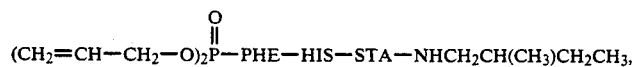
(CH₂=CH—CH₂—O)₂P(=O)—PHE—HIS—STA—NHCH₂CH(CH₃)CH₂CH₃,

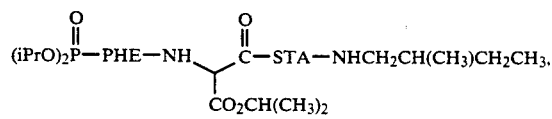
(iPrO)₂P(=O)—PHE—NH—CH(CO₂CH(CH₃)₂)—C(=O)—STA—NHCH₂CH(CH₃)CH₂CH₃,

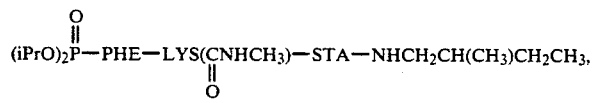
(iPrO)₂P(=O)—PHE—LYS(CNHCH₃)(=O)—STA—NHCH₂CH(CH₃)CH₂CH₃,

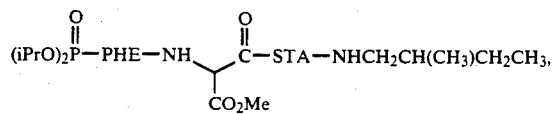
(iPrO)₂P(=O)—PHE—NH—CH(CO₂Me)—C(=O)—STA—NHCH₂CH(CH₃)CH₂CH₃,

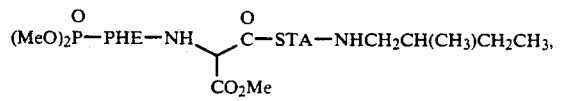
(MeO)₂P(=O)—PHE—NH—CH(CO₂Me)—C(=O)—STA—NHCH₂CH(CH₃)CH₂CH₃,

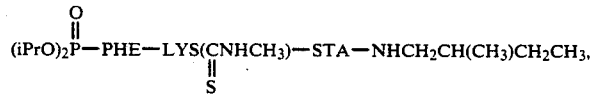
(iPrO)₂P(=O)—PHE—LYS(CNHCH₃)(=S)—STA—NHCH₂CH(CH₃)CH₂CH₃,

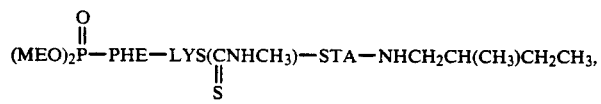
(MEO)₂P(=O)—PHE—LYS(CNHCH₃)(=S)—STA—NHCH₂CH(CH₃)CH₂CH₃,

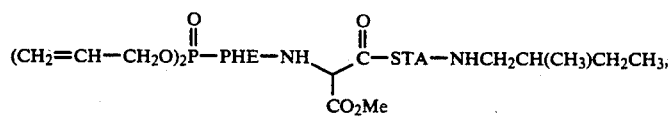
(CH₂=CH—CH₂O)₂P(=O)—PHE—NH—CH(CO₂Me)—C(=O)—STA—NHCH₂CH(CH₃)CH₂CH₃,

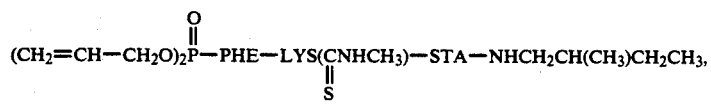
(CH₂=CH—CH₂O)₂P(=O)—PHE—LYS(CNHCH₃)(=S)—STA—NHCH₂CH(CH₃)CH₂CH₃,

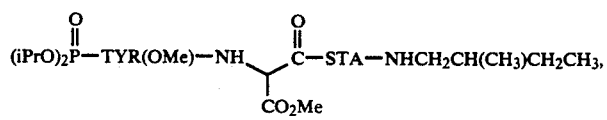
(iPrO)₂P(=O)—TYR(OMe)—NH—CH(CO₂Me)—C(=O)—STA—NHCH₂CH(CH₃)CH₂CH₃,

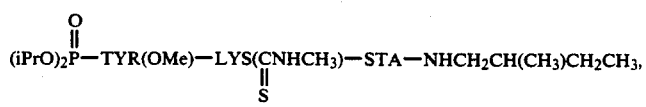
(iPrO)₂P(=O)—TYR(OMe)—LYS(CNHCH₃)(=S)—STA—NHCH₂CH(CH₃)CH₂CH₃,

-continued
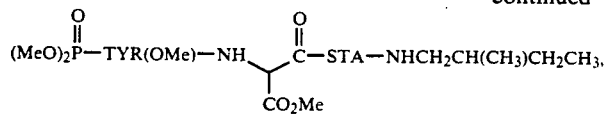
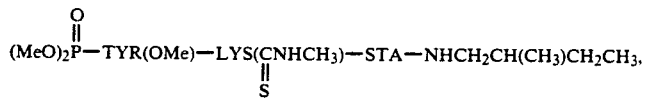
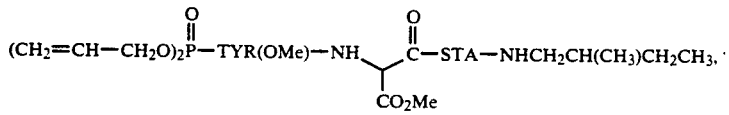
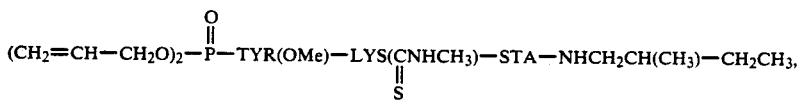
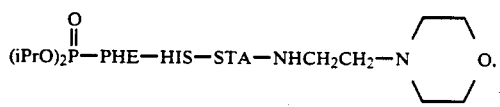
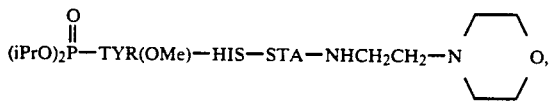
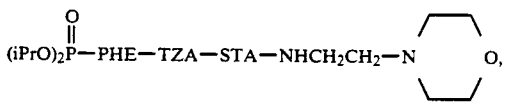
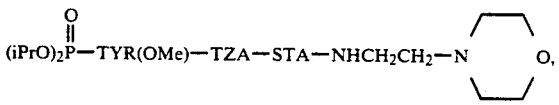
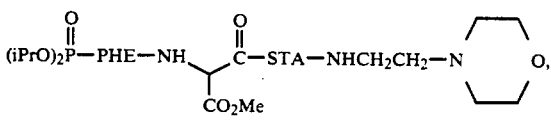
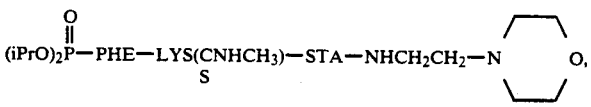
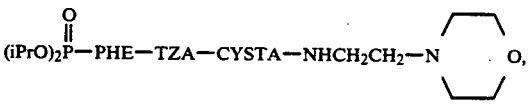
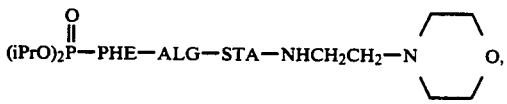
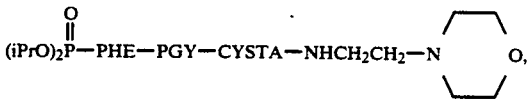

-continued

(iPrO)₂P(=O)—PHE—PGY—CYSTA—NHCH₂(CH₃)CH₂CH₃,

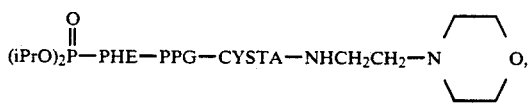(iPrO)₂P(=O)—PHE—PPG—CYSTA—NHCH₂CH₂—N(morpholino)O,

(iPrO)₂P(=O)—PHE—PPG—STA—NHCH₂CH(CH₃)CH₂CH₃

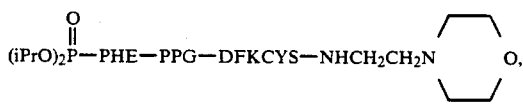(iPrO)₂P(=O)—PHE—PPG—DFKCYS—NHCH₂CH₂N(morpholino)O,

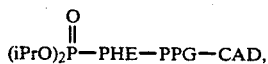(iPrO)₂P(=O)—PHE—PPG—CAD,

(iPrO)₂P(=O)—PHE—PPG—CDH,

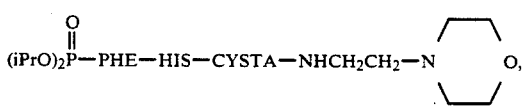(iPrO)₂P(=O)—PHE—HIS—CYSTA—NHCH₂CH₂—N(morpholino)O,

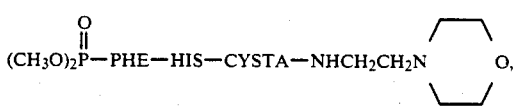(CH₃O)₂P(=O)—PHE—HIS—CYSTA—NHCH₂CH₂N(morpholino)O,

(iPrO)₂P(=O)—PHE—HIS—CYSTA—NHCH₂CH(CH₃)CH₂CH₃,

(MeO)₂P(=O)—PHE—PGY—CYSTA—NHCH₂CH(CH₃)CH₂CH₃,

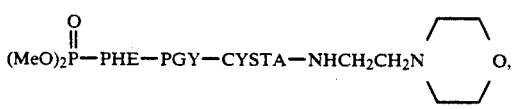(MeO)₂P(=O)—PHE—PGY—CYSTA—NHCH₂CH₂N(morpholino)O,

(iPrO)₂P(=O)—PHE—PGY—STA—NHCH₂CH(CH₃)CH₂CH₃,

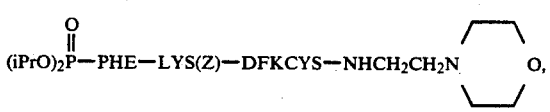(iPrO)₂P(=O)—PHE—LYS(Z)—DFKCYS—NHCH₂CH₂N(morpholino)O,

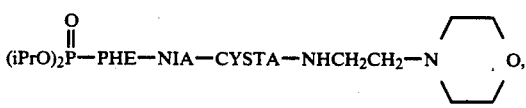(iPrO)₂P(=O)—PHE—NIA—CYSTA—NHCH₂CH₂—N(morpholino)O,

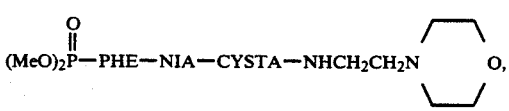(MeO)₂P(=O)—PHE—NIA—CYSTA—NHCH₂CH₂N(morpholino)O,

(MeO)₂P(=O)—PHE—HIS—CYSTA—NHCH₂CH(CH₃)CH₂CH₃,

(CH₂=CH—CH₂O)₂P(=O)—PHE—PGY—CYSTA—NHCH₂CH(CH₃)CH₂CH₃,

-continued
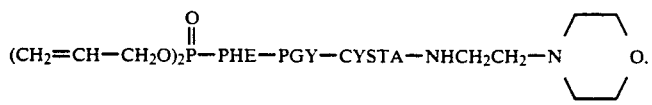
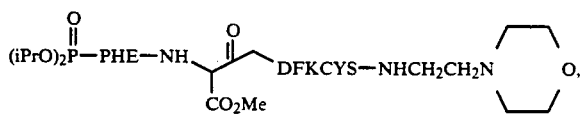
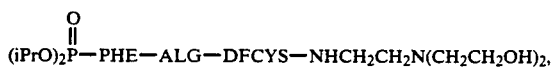
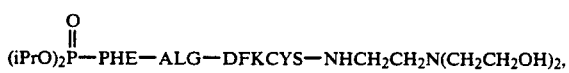
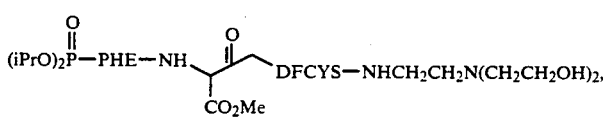
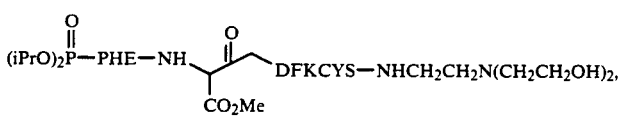
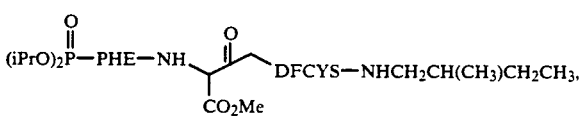
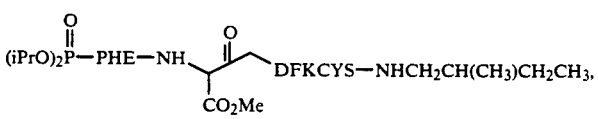
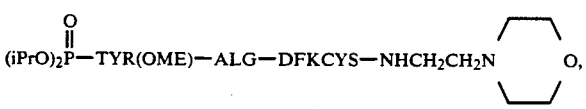

-continued (CH₂=CHCH₂O)₂P(=O)—TYR(OMe)—ALG—DFCYS—NHCH₂CH(CH₃)CH₂CH₃, (MeO)₂P(=O)—TYR(OMe)—ALG—DFKCYS—NHCH₂CH(CH₃)CH₂CH₃, (CH₂=CHCH₂O)₂P(=O)—TYR(OMe)—ALG—DFKCYS—NHCH₂CH(CH₃)CH₂CH₃, (CH₃O)₂P(=O)—PHE—NH—CH(CO₂Me)—CO—DFCYS—NHCH₂CH(CH₃)CH₂CH₃, (CH₂=CHCH₂O)₂P(=O)—PHE—NH—CH(CO₂Me)—CO—DFCYS—NHCH₂CH(CH₃)CH₂CH₃, (MeO)₂P(=O)—PHE—ATM—STA—NHCH₂CH(CH₃)CH₂CH₃, (MeO)₂P(=O)—PHE—ATM—CYSTA—NHCH₂CH(CH₃)CH₂CH₃, (MeO)₂P(=O)—PHE—ATM—CYSTA—NHCH₂CH₂N(morpholino), (MeO)₂P(=O)—PHE—ALG—DFCYS—NHCH₂CH(CH₃)CH₂CH₃, (MeO)₂P(=O)—PHE—ATM—CAD, (MeO)₂P(=O)—PHE—ATM—CDH, (MeO)₂P(=O)—PHE—ATM—DFCYS—NHCH₂CH₂N(morpholino), (MeO)₂P(=O)—PHE—ATM—DFKCYS—NH—CH₂CH₂N(morpholino), (MeO)₂P(=O)—PHE—ATM—DFCYS—NHCH₂CH(CH₃)CH₂CH₃, (MeO)₂P(=O)—PHE—ATM—DFKCYS—NHCH₂CH(CH₃)CH₂CH₃, (MeO)₂P(=O)—PHE—ALG—CDH, (MeO)₂P(=O)—PHE—ALG—CAD,

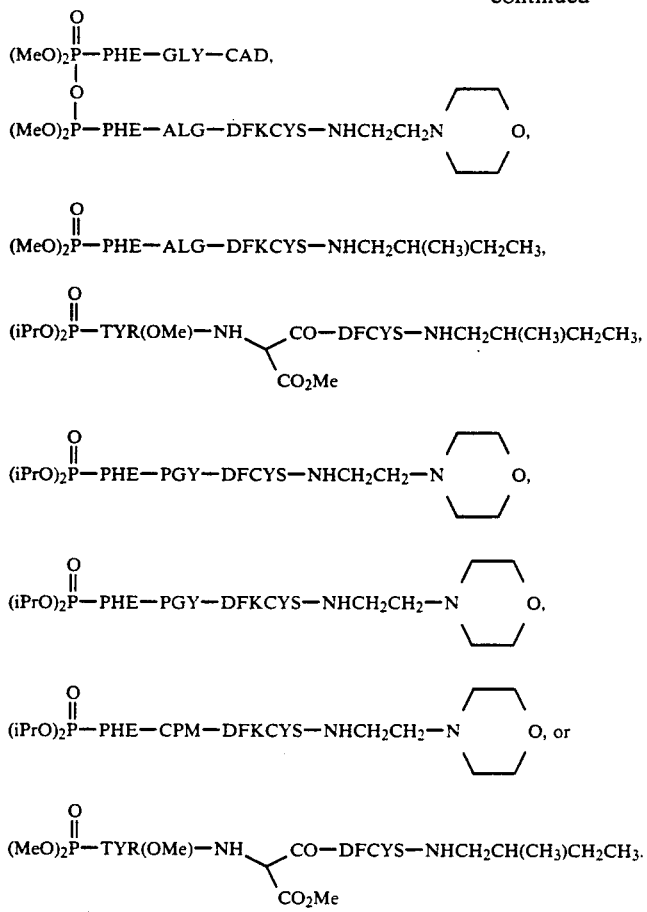
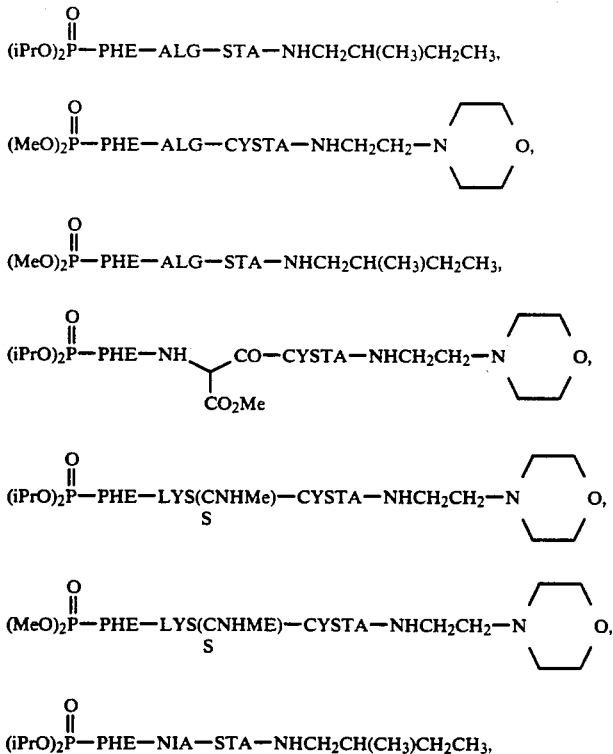
Most preferred compounds of the invention are:

-continued
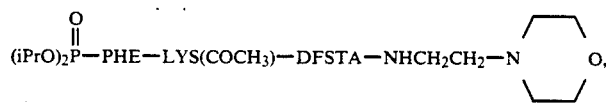
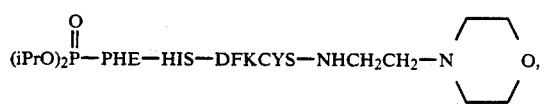
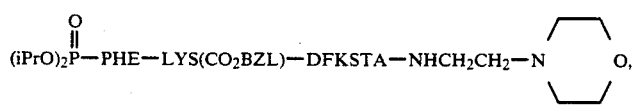
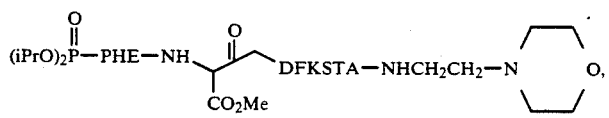
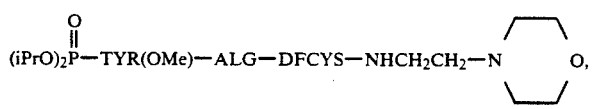
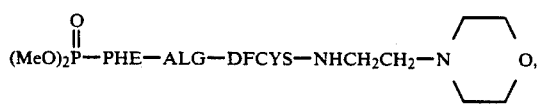
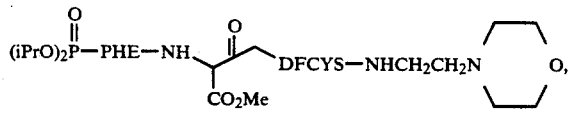
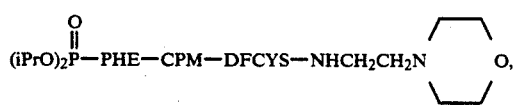
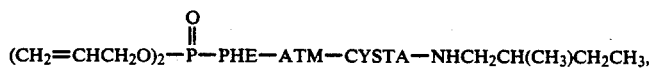
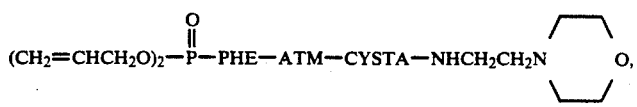

-continued
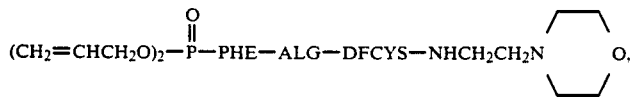
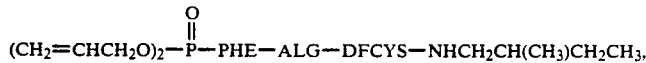
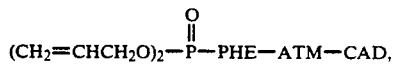
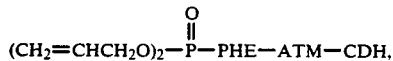
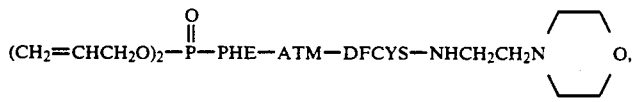
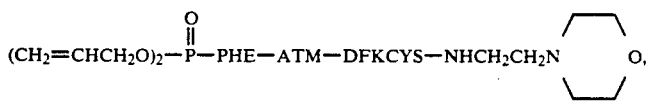
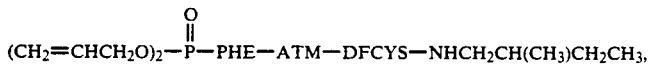
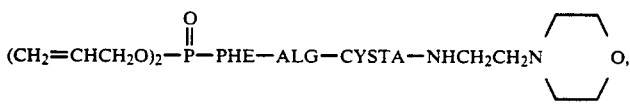
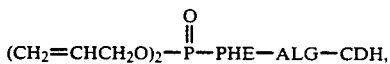
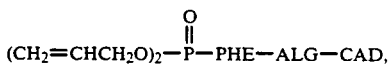
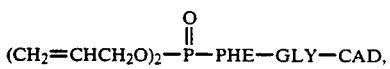
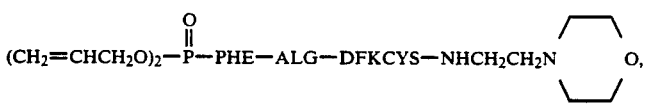
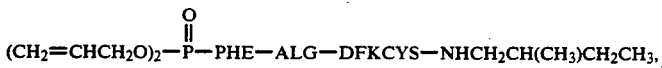
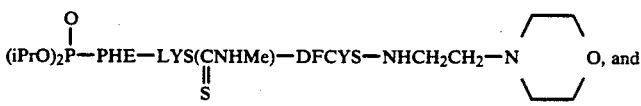
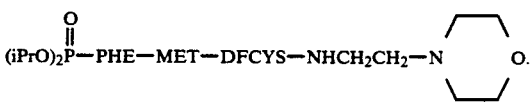
Still more preferred compounds include the following:

-continued (iPrO)$_2$P(=O)—PHE—ATM—CYSTA—NHCH$_2$CH(CH$_3$)CH$_2$CH$_3$, (iPrO)$_2$P(=O)—PHE—ATM—CYSTA—NHCH$_2$CH$_2$N(morpholino)O, (iPrO)$_2$P(=O)—PHE—ALG—DFCYS—NHCH$_2$CH$_2$N(morpholino)O, (iPrO)$_2$P(=O)—PHE—ALG—DFCYS—NHCH$_2$CH(CH$_3$)CH$_2$CH$_3$, (iPrO)$_2$P(=O)—PHE—ATM—CAD, (iPrO)$_2$P(=O)—PHE—ATM—CDH, (iPrO)$_2$P(=O)—PHE—ATM—DFCYS—NHCH$_2$CH$_2$N(morpholino)O, (iPrO)$_2$P(=O)—PHE—ATM—DFKCYS—NH—CH$_2$CH$_2$N(morpholino)O, (iPrO)$_2$P(=O)—PHE—ATM—DFCYS—NHCH$_2$CH(CH$_3$)CH$_2$CH$_3$, (iPrO)$_2$P(=O)—PHE—ATM—DFKCYS—NHCH$_2$CH(CH$_3$)CH$_2$CH$_3$, (iPrO)$_2$P(=O)—PHE—ALG—CYSTA—NHCH$_2$CH$_2$N(morpholino)O, (iPrO)$_2$P(=O)—PHE—ALG—CDH, (iPrO)$_2$P(=O)—PHE—ALG—CAD, (iPrO)$_2$P(=O)—PHE—GLY—CAD, (iPrO)$_2$P(=O)—PHE—ALG—DFKCYS—NHCH$_2$CH$_2$N(morpholino)O, (iPrO)$_2$P(=O)—PHE—ALG—DFKCYS—NHCH$_2$CH(CH$_3$)CH$_2$CH$_3$, and (iPrO)$_2$P(=O)—PHE—HIS—DFCYS—NHCH$_2$CH$_2$N(morpholino)O.

The compounds of the present invention have the advantage of increased hydrophilicity relative to renin inhibitors known in the art. This property makes the compounds more readily absorbed.

Additionally, they have been shown to decrease blood pressure when administered orally as well as intravenously. The compounds are often selective for the renin enzyme vs other aspartic proteases. Their chemical nature imparts greater ease of handling relative to similar compounds.

The compounds include solvates and hydrates and pharmaceutically acceptable acid addition salts of the basic compounds of formula I above.

The term pharmaceutically acceptable acid addition salt is intended to mean a relatively nontoxic acid addition salt either from inorganic or organic acids which would not cleave the phosphorous-nitrogen bond, such as, but not limited to acetic, citric, oxalic, malonic, salicylic, malic, benzoic, gluconic, fumaric, succinic, ascorbic, maleic, tartaric, methanesulfonic, and the like. The salts are prepared by contacting the free base form with a sufficient amount of the desired acid to produce a salt in the conventional manner. The free base forms may be regenerated by treating the salt form with a base. Unless otherwise specified the L form is the preferred embodiment.

The modified peptides of the present invention possess one or more chiral centers and each center may exist in the R(D) or S(L) configuration. The present invention includes all enantiomeric and epimeric forms as well as the appropriate mixtures thereof.

Some of the above novel peptides may be prepared in accordance with well-known procedures for preparing peptides from their constituent amino acids. Other of the novel peptides of the present invention are prepared by a stepwise procedure or by a fragment coupling procedure depending upon the particular final product desired.

The following scheme illustrates novel methods of preparing certain peptides of the present invention.

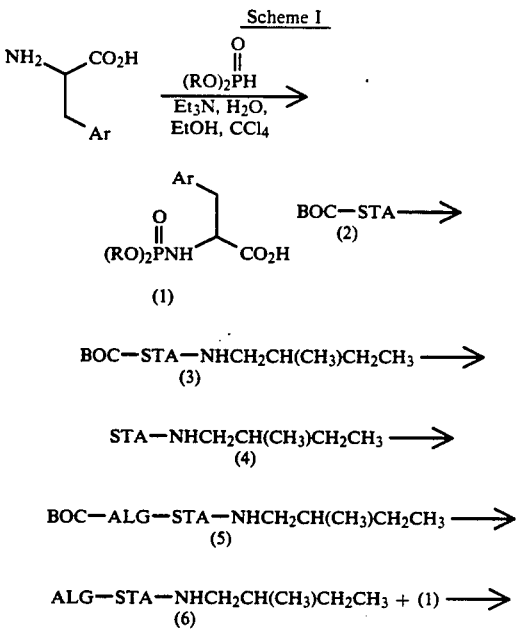

-continued
Scheme I

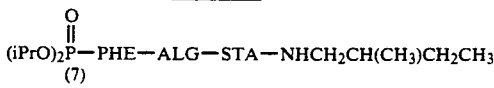

According to Scheme I above, BOC-protected statine (2) is reacted with DCC, HOBT, and a primary amine, for example, 2-methylbutylamine, to form the corresponding BOC-protected compound (3). The reaction takes place in an inert solvent such as methylene chloride, tetrahydrofuran, chloroform, dioxane, or ethyl acetate. The preferred solvent is methylene chloride. The reaction time varies from one to 24 hours. Preferably it takes about two to six hours. The reaction temperature may also vary from about 15° C. to 30° C. Preferably it is approximately 25° C.

The above compound (3) is reacted with a strong acid such as trifluoroacetic, HBr, or HCl to remove the BOC-protecting group thus forming corresponding compound (4) with a free amino terminus. Preferably HCl is used.

Compound 4 is then reacted with BOC-protected ALG to form the corresponding compound (5). This reaction takes place in an inert solvent, for example DMF, with DCC, HOBT, and triethylamine as activating agents at temperatures of from 0° C. to 25° C. The reaction may take as long as 72 hours.

This compound (5) is reacted with a strong acid, such as trifluoroacetic acid, to form the corresponding compound with a free amino terminus (6). The reaction takes place in an inert solvent, preferably dichloromethane, at about 25° C., taking from 0.5 to 2 hours.

The intermediate bisakoxyphosphinyl amino acid (1) can be made by the reaction of the appropriate amino acid with an equivalent amount of the bisalkoxyphosphite dissolved in CCl$_4$ in the presence of a base such as triethylamine and solvents to dissolve, for example, DMF, water and ethanol. The resulting compound (1) can then be coupled with other fragments (6) by methods standard in the art either sequentially or as a final reaction with previously linked fragments to afford the target compounds.

For compounds of the types illustrated in Examples 4, 5, 7, 8, and 9, other amino acid derivatives such as a protected HIS derivative (e.g. N$_{(\tau)}$-trityl, N$_{(\alpha)}$-Z), a BOC-protected ATM-Z, a BOC-protected ATM-TROC, a BOC-protected CYS(Z) or a BOC-protected aminomalonate monomethyl ester are substituted for the ALG derivative in the conversion of statine derivative (4) to depeptide (5). Additionally, other phosphonamide derivatives may be substituted for conversion of dipeptide (6) to tripeptide (7). The amides of CYSTA, CHSTA, DFSTA, DFCYS or DFCHS may replace STA amides. Finally, CAD or CDH may also replace STA amides.

This is shown in Scheme II.

Scheme II

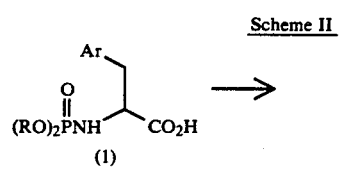

-continued
Scheme II

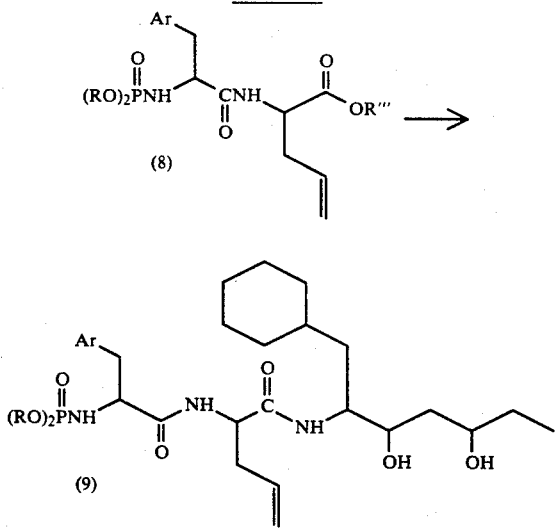

In this example, compound (1) is coupled with an ester of allylglycine to give (8); following saponification a subsequent coupling reaction utilizing CDH affords the final compound (9).

An alternative method of synthesis is shown in Scheme III wherein BOC-LYS(Z)-STA-NHCH$_2$CH(CH$_3$)CH$_2$CH$_3$ (10), prepared as in Scheme 1, is treated with hydrogen and palladium on carbon catalyst in an inert, polar solvent such as methanol to give the compound with a free amino side chain (11).

Acylation of this compound (11) with acylating agents such as in the final step of the previous method affords LYS-derivatized peptides such as the thiourea (12).

This compound (12) is treated with strong acid such as methanolic hydrogen chloride in an inert solvent, preferably dichloromethane, at about 25° C., taking 10 to 60 minutes to remove the BOC-protecting group.

The resulting compound (13) is reacted with an amino acid derivative such as I, DCC, and HOBT in a polar solvent such as DMF, at about 25° C., for 24 to 48 hours to form a compound of the present invention (14).

The DCC/HOBT method of coupling is well-known to those skilled in the art and is discussed in Chapter 5, "The Carbodiimide Method" by D.H. Rich and J. Singh in "The Peptides. Analysis, Synthesis, Biology," E. Gross and J. Meienhofer, Eds., Academic Press, New York, NY, 1979, pp. 42–44.

Peptide coupling depends on activating the carboxy terminus and condensing it with another peptide containing a free amino terminus. In addition to the DCC coupling method described above, other methods of activating the carboxyl group of a protected amino acid include:

1) The azide method—described in Chapter 4 of the above reference.
2) The mixed anhydride method—described in Chapter 6 of the above reference.
3) The active ester method—described in Chapter 3 of the above reference.

The invention includes a process for the preparation of compounds of formula I wherein A is

which comprises reacting a dialkyl phosphite with an aromatic amino acid as in X under basic, protic conditions to give a bisalkoxyphosphinyl amino acid, followed by coupling of the latter to the Y—W—V fragment and converting, if desired, to a pharmaceutically acceptable acid addition salt thereof by known means.

The compounds of the present invention are useful for treating renin-associated hypertension, congestive heart failure, hyperaldosteronism, glaucoma, and diseases caused by HTLV-I, -II, and -III viruses. They are also useful as diagnostic tools for determining the presence of renin-associated hypertension or hyperadosteronism.

The term lower alkyl refers to straight or branched chain alkyl radicals containing from 1 to 6 carbon atoms including but not limited to methyl, ethyl, n-propyl, isopropyl, n-butyl, iso-butyl, sec-butyl, 2-methylhexyl, n-penty, 1-methylbutyl, 2,2-dimethylbutyl, 2-methylpentyl, 2,2-dimethylpropyl, n-hexyl, and the like.

The term alkenyl refers to carbon groups of from two

Scheme III

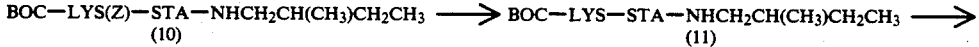

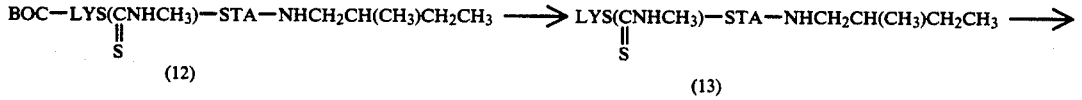

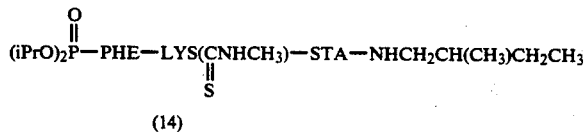

The strategy of peptides chain assembly and selection and removal of protecting groups is discussed in Chapter 1, "The Peptide Bond," in "The Peptides. Analysis, Synthesis, Biology," E. Gross and J. Meienhofer, Eds., Academic Press, New York, NY, 1979, pp. 42–44.

to about six carbon atoms containing a double bond such as, but not limited to: vinyl, allyl, methylallyl, and the like.

The term benzyl refers to unsubstituted or substituted benzyl, the substituents are, for example, halogen or hydroxy.

Pharmaceutical compositions which comprise an effective amount of the compound in combination with a pharmaceu-tically acceptable carrier are part of the present invention. An important aspect of the present invention is a method of treating renin-associated hypertension in a mammal which comprises administering a pharmaceutical composition containing an effective amount of a compound of the invention in combination with a pharmaceutically acceptable carrier to the mammal.

Another equally important aspect of the present invention is a method of treating hyperaldosteronism in a mammal which comprises administering a pharmaceutical composition containing an effective amount of a compound of the invention in combination with a pharmaceutically acceptable carrier to the mammal.

An additional aspect of the present invention is a method for treating congestive heart failure in a mammal which comprises administering a pharmaceutical composition containing an effective amount of a compound in combination with a pharmaceutically acceptable carrier to the mammal.

The effectiveness of the aforementioned compounds is determined by a test for in vitro renin inhibitory activity. This activity is determined by a standard radioimmunoassay for angiotensin I. In this assay the enzyme, renin, incubated for two hours at 37° C. in the presence of a substrate, angiotensinogen, generates the product, angiotensin I. Test compounds are added to the incubation mixture. Relative activity is reported as the $IC_{50}$, which is the molar concentration of test compound causing a 50% inhibition of the renin activity.

TABLE 2

| Compound | $IC_{50}$ (M) |
|---|---|
| (iPrO)$_2$P(=O)—PHE—ALG—CYSTA—NHCH$_2$CH$_2$N(morpholino) | $0.97 \times 10^{-9}$ |
| (iPrO)$_2$P(=O)—PHE—ALG—CAD | $0.67 \times 10^{-9}$ |
| (iPrO)$_2$P(=O)—TYR(OMe)—ALG—CAD | 92% inhib @ $10^{-8}$ M |
| (iPrO)$_2$P(=O)—PHE—ATM—CYSTA—NH(CH$_2$CH$_2$OH)$_2$ | $5.05 \times 10^{-9}$ |
| (iPrO)$_2$P(=O)—PHE—ATM—CAD | $0.91 \times 10^{-9}$ |
| (iPrO)$_2$P(=O)—PHE—GLY—CAD | $6.98 \times 10^{-9}$ |
| (iPrO)$_2$P(=O)—PHE—ATM—DFKCYS—NHCH$_2$CH$_2$N(morpholino) | |
| (iPrO)$_2$P(=O)—PHE—HIS—DFCYS—NHCH$_2$CH$_2$N(morpholino) | 53% inhib @ $10^{-8}$ M |
| (iPrO)$_2$P(=O)—PHE—ATM—DFCYS—NHCH$_2$CH$_2$N(morpholino) | |

As can be seen from the above table, the compounds of the present invention have a significant effect on the activity of renin and thus are useful for the treatment of hypertension, hyperaldosteronism, and congestive heart failure. The compounds of the present invention are also useful for treating diseases caused by retroviruses, for example, HTLV-I -II, and -III.

Oral efficacy is determined by elevating basal plasma renin activity in normotensive monkeys which have been have been given furosemide prior to dosing with a test compound, L-Norvalinamide,N-bis(1-methylethoxy)phosphinyl]-L-phenylalanyl-N-[1-cyclohexylmethyl]-2,3-dihydroxy-5methylhexyl]-4,5-didehydro-, [1S-(1R*,2S*,3R*)]-.

On the test day monkeys are removed from their home cage, placed in the restraining device, and moved to a quiet room for blood pressure monitoring. Monkeys are allowed to acclimate for at least 60 minutes. A control blood sample is taken, and then either vehicle or test compound is given by the oral or intravenous route. Blood pressure is monitored continuously. Up to ten blood samples are taken for PRA determinations at appropriate times after dosing.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders, or tablet disintegrating agents; it can also be encapsulating material. In powders, the carrier is a finely divided solid which is in admixture with the finely divided active compound. In the tablet the active compound is mixed with carrier having the necessary binding properties in suitable proportions and compacted in the shape and size desired. The powder and tablets preferably contain from 5 to 10 to about 70 percent of the active ingredient. Suitable solid carriers are magnesium carbonate, magnesium stearate, talc, sugar, tragacanth, methylcellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

The compound of the present invention may be administered orally, buccally, parenterally, by inhalation spray, rectally, or topically in dosage unit formulations containing conventional nontoxic pharmaceutically acceptable carriers, adjuvants and vehicles as desired. The term parenteral as used herein includes subcutaneous injections, intravenous, intramuscular, intrasternal injection, or infusion techniques.

For preparing suppositories, a low melting wax such as a mixture of fatty acid glycerides or cocoa butter is first melted, and the active ingredient is dispersed homogeneously therein by stirring. The molten homogeneous mixture is then poured into convenient sized molds, allowed to cool, and thereby solidify.

Liquid form preparations include solutions, suspensions, and emulsions. As an example may be mentioned water or water/propylene glycol solutions for parenteral injection. Liquid preparations can also be formulated in solution in aqueous polyethyleneglycol solution. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dosage form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol, and the like, as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampules. The unit dosage form can also be a capsule, cachet, or tablet itself, or it can be the appropriate number of any of these in packaged form.

The quantity of active compound in a unit dose of preparation may be varied or adjusted from 1 mg to 500 mg, preferably 5 to 100 mg according to the particular application and the potency of the active ingredient. The compositions can, if desired, also contain other compatible therapeutic agents.

In therapeutic use as renin inhibitors, the mammalian dosage range for a 70 kg subject is from 1 to 1500 mg/kg of body weight per day or preferably 25 to 750 mg/kg of body weight per day optionally in divided portions. The dosages, however, may be varied depending upon the requirements of the patient, the severity of the condition being treated and the compound being employed. Determination of the proper dosage for a particular situation is within the skill of the art. Generally, treatment is initiated with small dosages which are less than the optimum dose of the compound. Thereafter the dosage is increased by small increments until the optimum effect under the circumstances is reached For convenience, the total daily dosage may be divided and administered in portions during the day if desired.

The following examples are provided to enable one skilled in the art to practice the present invention. These examples are not intended in any way to limit the scope of the invention but are illustrative thereof.

EXAMPLE 1

A solution of BOC—ALG—CYSTA—AEM (1.5 g, 2.9 mmole) in $CH_2Cl_2$ (20 m) and trifluoroacetic acid (TFA) (10 ml) was stirred at room temperature for two hours. After concentrating, the residue was dissolved in $CH_2Cl_2$ and concentrated again. The residue was taken up in $CH_2Cl_2$ and treated with HCl (g) for 10 minutes. After concentrating, the residue was taken up in DMF (20 ml) and treated with $(iPr)_2NEt$ until basic. The solution was added to an ice cold mixture of

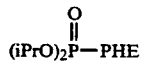

(0.94 g, 2.9 mmole), HOBT.$H_2O$ (0.41 g, 3.0 mmole), DCC (0.63 g, 3.0 mmole), and DMF (10 ml). The mixture was stirred overnight at room temperature. After filtering, the filtrate was concentrated under high vacuum. The residue was taken up in CHCl₃ and washed with saturated NaHCO₃. The solution was dried over Na₂SO₄ and concentrated to yield 3.02 g of a foam. Purification by flash chromatography on silica gel afforded 1.18 g of a foam. MS (FAB) 736.4(m+1).

In a like manner were prepared:

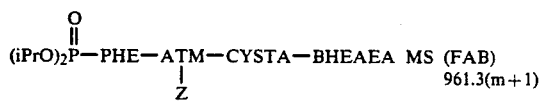 MS (FAB) 961.3(m+1)

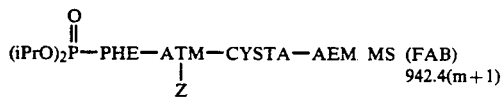 MS (FAB) 942.4(m+1)

EXAMPLE 2

A solution of BOC—ALG—CAD (1.25 g, 2.8 mmole) in CH₂Cl₂ (20 ml) and TFA (7 ml) was stirred for two hours at room temperature. After concentration, the residue was taken up in CH₂Cl₂ and concentrated again. The residue was dissolved in CH₂Cl₂ and treated with HCl (g) for 10 minutes. The solution was concentrated and dried under high vacuum. Residue was taken up in DMF (20 ml) and treated with (iPr)₂NEt until basic and added to an ice cold mixture of

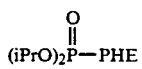

(0.93 g, 2.8 mmole), HOBT.H₂O (0.41 g, 3.0 mmole), DCC (0.62 g, 3.0 mmole), and DMF (10 ml). The mixture was stirred overnight at room temperature. After filtering, the filtrate was concentrated under high vacuum. The residue was taken up in CHCl₃ and washed with 1N citric acid, brine, saturated NaHCO₃, and brine. The solution was dried over Na₂SO₄ and concentrated to yield 1.47 g of a solid which was purified by flash chromatography on silica gel to give 1.14 g of a white solid. MS (FAB) 652.4(m+1).

EXAMPLE 3

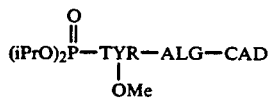

A solution of BOC—ALG—CAD (1.9 g, 4.3 mmole) in CH₂Cl₂ (50 ml) and MeOH (5 ml) was treated with HCl (g) for 10 minutes and was stirred at room temperature for two hours. After concentrating, the residue was taken up in DMF (30 ml) and treated with (iPr)₂NEt until basic. The solution was then added to an ice cold solution of

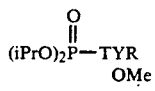

(1.55 g), 4.3 mmole), HOBT.H₂O (0.61 g, 4.5 mmole), DCC (0.94 g, 4.5 mmole), and DMF (10 ml). The mixture was stirred in an ice bath for two hours and then overnight at room temperature. After filtering, the filtrate was concentrated under high vacuum. The residue was dissolved in CHCl₃ and washed with 1N citric acid, brine, saturated NaHCO₃, and brine. The material was dried over Na₂SO₄ and concentrated to a paste which was purified by flash chromatography on silica gel to yield 1.4 g of a foam. MS (FAB) 682.4(m+1)

EXAMPLE 4

A solution of

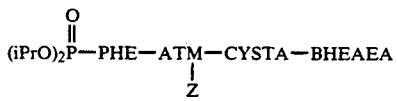

(0.58 g, 0.6 mmole) and p-toluenesulfonic acid (0.29 g, 1.51 mmole) in MeOH (20 ml) was treated with 0.3 g of 20% Pd/C catalyst. The mixture was stirred under a H₂ atmosphere for six hours. The solution was filtered through celite to remove catalyst and then concentrated. The residue was taken up in EtOAc and washed with saturated NaHCO₃ (twice) and brine. After drying over Na₂SO₄, concentration gave 0.46 g of material which was flash chromatographed on silica to yield 0.17 g of a film. MS (FAB) 826 5(m+1).

EXAMPLE 5

0.30 g (1 mmol) GLY—CAD, 0.33 g

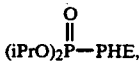

0.21 g DCC, 0.14 g HOBT, and 0.24 g dimethylaminopyridine were combined in methylene chloride at 0°, then allowed to come to ambient temperature over 18 hours. The reaction mixture was filtered, then washed sequentially with 5% aqueous citric acid, saturated NaHCO₃, saturated NaCl, then dried (MgSO₄), and concentrated. After chromatography (silica gel, eluting with 95% ethyl acetate 5% methanol) 0.36 g of the product was collected. The white foam, m.p. 80°-82° analyzed Calc'd: C, 60.86; H, 8.90; N, 6.87,
Found: C, 60.56; H, 8.79; N, 6.75.
and showed an m/e peak =612 in the mass spectrum analysis.

EXAMPLE 6

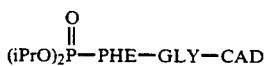

0.33 g

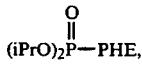

0.30 g GLY-CAD, 0.21 g DCC, 0.14 g HOBT, and 0.24 g DMAP were combined in methylene chloride at 0° C., then allowed to warm to ambient temperature over 18 hours. The reaction mixture was filtered, the filtrate washed consecutively with 5% citric acid, sat. NaHCO$_3$, sat NaCl, dried over MgSO$_4$, filtered and concentrated to yield a white foam. This was purifed by chromatography on SiO$_2$, eluting with ethyl acetate with a gradient increase to 5% methanol 95% ethyl acetate. The product (0.36g, 59%) was isolated as a white foam m.p. 80–82. Anal.: Calc'd: C, 60.86; H, 8.90; N, 6.87; Found: C, 60.56, H, 8.79; N, 6.75 MS 612(m+1).

EXAMPLE 7

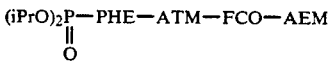

To the TROC-aminothiazole alcohol (4.57 g, 14.42 mmol) in dichoromethane (60 ml) and DMSO (10 ml) at 0° C. was added dichloroacetic acid (0.53 ml, 6.63 mmol) followed by dicyclohexylcarbodiimide (9.12 g, 44.2 mmol) and the resulting mixture stirred at 0° C. for one hour before warming to room temperature and stirring for a further 20 hours. Oxalic acid (9 g) in methanol (125 ml) was added slowly and the reaction stirred for 30 minutes before filtration and evaporation. The crude residue was taken up in ethyl acetate (15 ml), refiltered, and evaporated.

The crude product was dissolved in THF/MeOH (100 ml/20 ml) followed by addition of excess NH$_4$Cl (3 g) and activated zinc dust (1.0 g, 325 mesh). After stirring for ca 30 hours the reaction mixture was filtered and evaporated. The residue was taken up in 20% aqueous phosphoric acid (200 ml) and washed twice with 50-ml portions of ethyl acetate. The organic layer was dried (Na$_2$SO$_4$) and evaporated to afford crude starting material (TROC-material) which could be resubjected to the deprotection conditions. The aqueous layer was brought to pH 4 with addition of NH$_4$OH at 0° C. (slowly). The product was extracted from the aqueous layer by washing with ethyl acetate several times. The organic extracts were dried (Na$_2$SO$_4$) and evaporated to an orange oil. Purification by column chromatography on silica gel eluting with 5→15% methanol in chloroform afforded product as a yellowish foam (0.5 g). Mass spectrum (MS m/e) 841.7 (m+1); Ana. calculated for C$_{38}$H$_{58}$N$_7$O$_8$SF$_2$P.

EXAMPLE 8

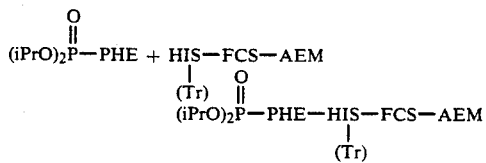

To the acid (0.65 g, 1.88 mmol) in dry DMF (10 ml) with HOBT (0.25 g, 1.88 mmol) was added DCC (0.39 g, 1.88 mmol) in DMF (5 ml) at 0° C. After five minutes the amine (1.40 g, 1.88 mmol) in DMF (10 ml) was added and the whole stirred for one hour at 0° C. before warming to room temperature and stirring overnight. The precipitated DCU was removed by filtration and the DMF evaporated under reduced pressure. The crude residue was diluted with ethyl acetate and washed with saturated NaHCO$_3$ solution followed by brine. Drying (Na$_2$SO$_4$) and concentration under reduced pressure gave the crude product as a yellowish semi-solid. Purification by column chromatography on silica gel eluting with 5% methanol in ethyl acetate afforded a white foam (1.30 g, 64.4%); mass spectrum FAB m/e 1054.8 (m+1); 812.3 (MH⊕-Cϕ$_3$); NMR agreed with structure-single isomer.

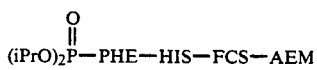

The trityl-protected amine (300 mg, 0.288 mmol) was heated in 80% aqueous acetic acid (5 ml) at 80°–90° C. for five minutes. Evaporation under reduced pressure gave a crude residue which was taken up in ethyl acetate and washed with saturated sodium bicarbonate solution. Drying (Na$_2$SO$_4$) and column chromatography on silica gel eluting with a gradient of 5→15% methanol in CHCl$_3$ gave the title compound as a white foam (0.15 g). The solid was dissolved in methanol (2 ml) and distilled methanesulphonic acid (24 μl) was added. After stirring for 10 minutes and evaporation the residue was dissolved in H$_2$O and freeze-dried. The structure of the bis-methanesulphonic acid salt (0.16 g) as a white fluffy solid was confirmed by spectral data; mass spectrum FAB (m+1) 812.4 (mw=1129.80).

Anal. for C$_{38}$H$_{60}$N$_7$O$_8$F$_2$P.2CH$_3$SO$_3$H.3-H$_2$O.0.6HCl$_3$: Calcd: C, 46.19; H, 6.56; N, 9.29; Found: C, 46.13; H, 6.88; N, 8.58.

(HPLC: single peak t$_R$=13 minutes)

EXAMPLE 9

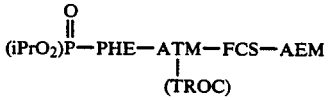

To the acid

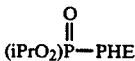

+(2.05 g, 5.96 mmol) and HOBT (0.805 g, 5.96 mmol) in dry DMF (30 ml) at 0° C. was added DCC (1.23 g, 5.96 mmol) in DMF (10 ml). After stirring for five minutes the amine

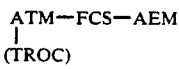
(4.21 g, 5.96 mmol) in DMF (20 ml) was added and the reaction stirred for a further hour at 0° C. before warming to room temperature and stirring overnight. The precipitated DCU was removed by filtration and the DMF evaporated under reduced pressure. The crude residue was taken up in ethyl acetate and washed with saturated NaHCO$_3$ and brine. After drying (Na$_2$SO$_4$) the product was purified by column chromatography on silica gel, eluting with 5% methanol in dichloromethane to afford the title compound as a yellowish foam (5.50 g, 89.3%); FAB m/E 1020.3 (m+1); (thioglycerol).

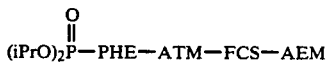

To the TROC-protected aminothiazole derivative (1 g, 0.97 mmol) in THF (40 ml) and methanol (10 ml) at room temperature was added solid ammonium chloride (1 g) and activated zinc dust (325 mesh, 0.13 g). The resulting suspension was stirred rapidly for three hours. Further zinc (0.26 g) was added and the reaction stirred for 30 hours. After filtration and evaporation the crude residue was purified by column chromatography on silica gel, eluting with 5→15% methanol in chloroform to afford 429 mg white foam confirmed as the correct product by NMR and mass spectroscopy; FAB MS (m/e) 844.0 (m+1).

Anal. for C$_{38}$H$_{60}$N$_7$O$_8$SF$_2$P.0.4M CHCl$_3$): Calcd.: C, 51.72; H, 6.83; N, 11.00; S, 3.60, Found: C, 51.82; H, 6.91; N, 10.87; S, 3.85.

INTERMEDIATE FOR ALL EXAMPLES

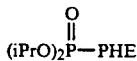

The intermediate N-(diisopropyloxyphosphoryl)phenyl alanine is prepared as described in *Synthesis* 444 (1988). An ice cold mixture of PHE (3.30 g, 0.02 mole) in Et$_3$N (10 m), H$_2$O (6 ml), and EtOH (4 ml) was treated dropwise with diisopropyl phosphite (3.32 ml, 0.02 mole) in CCl$_4$ (8 ml) and stirred overnight at room temperature. The mixture was acidified to pH 2 with 1N HCl and extracted with EtOAc. The extract solution was dried over Na$_2$SO$_4$ and concentrated to yield 5.63 g of an oil which solidified on standing.

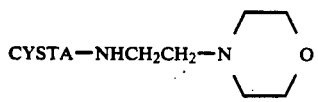

A solution of

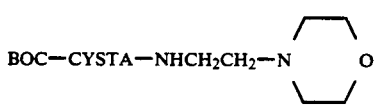

(10 g) in CH$_2$Cl$_2$ (250 ml) was treated with methanolic HCl (250 ml) and stirred for two hours at 25° C. The resulting solution was evaporated and the residue was treated with a saturated solution of ammonia in CH$_2$Cl$_2$ (300 ml). After 10 minutes of vigorous stirring, NH$_4$Cl was removed by filtration and the filtrate was evaporated to give the product as a solid.

The following compounds are prepared in an analogous manner:

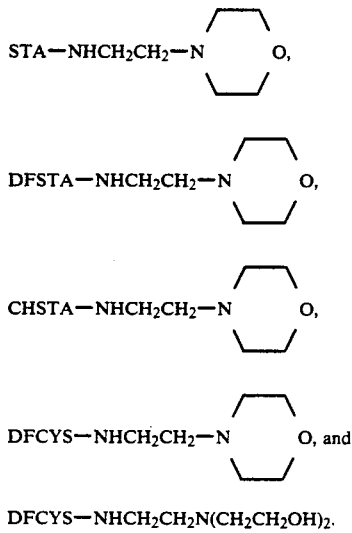

DFCYS—NHCH$_2$CH$_2$N(CH$_2$CH$_2$OH)$_2$.

CYSTA—BHEAEA

A solution of

compound (22.33 g, 42.2 mmole) in CH$_2$Cl$_2$ (575 ml) and MeOH (160 ml) was treated with HCl (g) for 10 minutes and stirred in an ice bath for 30 minutes before concentrating. The residue was taken up in CH$_2$Cl$_2$ (450 ml) and cooled in an ice bath. The cold solution was treated in portions with an ice cold solution of CH$_2$Cl$_2$ (700 ml) which had been saturated with NH$_3$(g). A precipitate formed as the mixture stirred for one hour. After filtering, the filtrate was concentrated to yield 14.05 g of a gold oil.

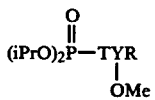

An ice cold suspension TYR—OMe.HCl (2.317 g, 0.01 mmole) in Et$_3$N (5 ml), H$_2$O (3 ml), and EtOH (2 ml) was treated with diiospropyl phosphite (1.66 ml, 0.01 mmole) in CCl$_4$ (4 ml). The mixture was stirred overnight at room temperature. After treating with 1N HCl until pH 2, the mixture was extracted with EtOAc (three times). The organic layer was dried over Na$_2$SO$_4$ and concentrated to yield 3.22 g of a film. The structure was supported by MS and NMR.

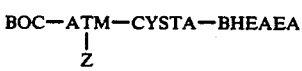

A solution of BOC—ATM(Z) (5.0 g, 11.9 mmole) in DMF (25 ml) was cooled in an ice bath and treated with HOBT.H$_2$O (1.68 g, 12.5 mmole), DCC (2.6 g, 12 5 mmole), and CYSTA—BHEAEA (4.1 g, 11.9 mmole) in DMF (25 ml). The mixture was stirred overnight at room temperature. After filtering, the filtrate was concentrated under high vacuum. The residue was taken up in EtOAc and washed with saturated NaHCO$_3$ and brine. After drying over Na$_2$SO$_4$, the solution was concentrated to yield 9.13 g of a foam which was flash chromatographed on silica to yield 3.26 g of a foam.

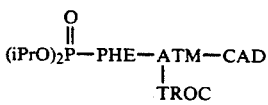

A solution of BOC—ATM (TROC)-CAD (2.65 g, 3.85 mmole) in CH$_2$Cl$_2$ (150 ml) and MeOH (25 ml) was treated with HCl (g) for 10 minutes and then stirred for two hours. The solution was concentrated, taken up in DMF (30 ml), and treated with (iPr)$_2$NEt until basic. The solution was added to an ice cold solution solution of

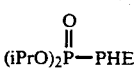

1.27 g, 3.85 mmole), HOBT.H$_2$O (0.55 g, 4.04 mmole), and DCC (0.84 g, 4.04 mmole) in DMF (10 ml). The mixture was stirred overnight at room temperature. After filtering, the filtrate was concentrated under high vacuum. The residue was dissolved in CHCl$_3$ and washed with 1N citric acid, brine, saturated NaHCO$_3$, and brine. The solution was dried over Na$_2$SO$_4$ and concentrated to yield 3.67 g of a foam. Purification by flash chromatography on silica gel afforded 1.9 g of a foam. MS (FAB) 900.2(m+1).

Removal of the TROC protecting group from the penultimate target is achieved by stirring the compound in acetic acid with zinc dust; the solution is filtered and concentrated to give the product as the acetate salt. This can be converted to the free base to afford compounds identical in all respects to those made using the Z protecting group.

BOC—ATM(Z)

Prepared in a similar manner as BOC—ATG(Z) from ATM.2HCl as in reference Chem Ber., Vol. 97, p 1767 (1964).

BOC—ATM(Z)—CAD

The compound was prepared as in Example 1 from BOC—ATM(Z) (6.3 g), HOBT H$_2$O (2.02 g), DCC (3.1 g), CAD.HCl (4.19 g) and Et$_3$N (1.5 g). This gave 5.7 g of the product as a mixture of diastereomers as a white foam, mp 95°-100° C. The structure was confirmed by NMR and mass spectroscopy.

ATM(Z)—CAD

The compound was prepared by saturating a solution of BOC—ATM(Z)-CAD (5.35 g) in CH$_2$Cl$_2$ (70 ml) and MeOH (10 ml) with HCl gas. The solution was stirred at room temperature for 2 hours and then evaporated in vacuo to dryness. The residue was dissolved in EtOAc (75 ml) and washed successively with saturated NaHCO$_3$ (2×100 ml) and saturated salt solution (100 ml). The organic phase was dried over MgSO$_4$ and evaporated in vacuo to give 3.8 g of product as a mixture of diastereomers as a light yellow foam, mp 84°-91° C. The structure was confirmed by NMR and mass spectroscopy.

BOC—ATM(Z)—CYSTA—AEM

The compound was synthesized as in Example 1 from BOC—ATM(Z) (4.21 g), HOBT.H$_2$O (1.35 g), DCC (2.06 g), and CYSTA—AEM (3.27 g). This gave 4.6 g of product as a mixture of diastereomers as a white foam, mp 97°-100° C. The structure was confirmed by NMR and mass spectroscopy.

BOC—(S)ATM—OBZL.HCl

N—BOC—Aspartic acid α-benzyl ester (40 g, 0.124 mol) in EtOAc (1 L) was treated at 0° C. with N-methylmorpholine (13.8, g, 0.1376 mol) and isobutyl chloroformate (18.6 g, 0.136 mol). The mixture was stirred at 0°-10° C. for three hours. The mixture was filtered free of precipitate and treated with a solution of diazomethane [(~0.175 mol) freshly distilled from Diazald® (53 g)] in ether (~500 ml). The mixture was stirred for 16 hours under a N$_2$ stream. The solution was washed with saturated salt solution (500 ml) and evaporated in vacuo to give the diazoketone as a dark oil. This oil was dissolved in ether (400 ml) and carefully treated with HCl gas. The gas treatment stopped when the pH of the solution reached 2 (wet litmus), approximately two to eight minutes. The solution was then immediately treated with a solution of saturated sodium bicarbonate (600 ml). The organics were washed with saturated salt solution (200 ml) and dried over MgSO$_4$. The organics were evaporated in vacuo to give 44.4 g of the chloroketone as a tan solid. This was dissolved in acetone (225 ml) and treated in portions with thiourea (7.6 g, 0.1 mol). The solution was stirred at room temperature for 24 hours. The mixture was filtered to collect solid, the solid washed with acetone (2×75 ml), and dried in vacuo to give 20.6 g of product as a white solid, mp =144°-146° C. The structure was confirmed by NMR and mass spectroscopy.

BOC—(S)ATM—CAD

To BOC—(S)—ATM—OBZL.HC (2.06 g) in methanol (35 ml) was added a solution of NaOH (0.6 g) in water (10 ml). The solution was stirred at room temperature for four hours and then taken to pH 6 (wet litmus) with 1N HCl. The solution was evaporated in vacuo and dissolved in DMF (20 ml). This solution was treated at 0° C. sequentially with Et$_3$N (1.51 g), HOBT (0.667 g), DCC (1.03 g), and CAD (1.22 g). The mixture was stirred for 72 hours The mixture was filtered free of solids and the solvent evaporated in vacuo. The residue from evaporation was dissolved in EtOAc (100 ml) and washed sequentially with saturated sodium bicarbonate (100 m) and saturated salt solution. The organics were dried over MgSO$_4$ and evaporated in vacuo to give a yellow foam. The foam was chromatographed over silica gel to give the product as a white solid, 1.2 g. The structure was confirmed by NMR and mass spectroscopy.

(S)ATM—CAD.2HCl

To BOC—(S)—ATM—CAD (1.1 g) in a mix of CH$_2$Cl$_2$ (75 ml) and MeOH (15 ml) was added HCl (gas) and the solution stirred at room temperature for three hours The solution was evaporated in vacuo to give the product, which was used without further purification. The structure was confirmed by NMR and mass spectroscopy.

BOC—GLY—CAD

A solution of 2.66 g (15.2 mmole) of BOC—GLY, 2.2 g (15.9 mmole) of HOBT.H$_2$O, 4.25 g (15.2 mmole) of CAD.HCl, and 2.16 ml (15.5 mmole) of Et$_3$N in 40 ml DMF was cooled in ice and treated with 3.32 g (15.9 mmole) of DCC in 5 ml DMF. After two hours at 0° C., the mixture was allowed to stir at room temperature for 24 hours. The mixture was filtered and the filtrate concentrated under high vacuum. The residue was taken up in EtOAc and washed with H$_2$O, 1N citric acid, saturated NaHCO$_3$, and saturated NaCl. Drying and removal of the solvent under reduced pressure gave the crude product. Chromatography on silica gel, eluting with CHCl$_3$/MeOH (97.5/2.5) gave 6.6 g of the product The structure was confirmed by NMR and mass spectroscopy.

GLY—CAD.HCl

A solution of 6.62 g (16.5 mmole) of BOC—GLY—CAD in 60 ml CH$_2$Cl$_2$ was treated with 30 ml of TFA and stirred at room temperature for two hours. The solvent was removed under reduced pressure, CH$_2$Cl$_2$ added, and the solvent removed again. The residue was then taken up in CH$_2$Cl$_2$ and HCl gas bubbled in. Removal of the solvent under reduced pressure gave the product. The material was used in the next reaction without purification.

BOC—ALG

ALG was prepared according to the procedure described in the *Journal of the American Chemical Society*, Vol. 109, pp. 4649–4659, 1987. A solution of ALG (9.16 g) in a mixture of dioxane (150 ml) and 2N NaOH (70 ml) was treated with di-t-butyldicarbonate (34 g). The mixture was stirred overnight, basified to pH 8.5 with 2N NaOH, diluted with water and extracted with ether. The aqueous solution was acidified with citric acid and extracted twice with ether. The combined ether extracts were washed with brine, dried over Na$_2$SO$_4$ and concentrated to yield BOC—ALG as a solid. MS (CI, CH$_4$) 216(m+1).

BOC—DFCYS

Activated Zn dust (9.2 g) was suspended in dry THF (300 ml) under N$_2$. A crystal of iodine was added and the mixture was heated to reflux. Ethyl bromodifluoroacetate (0.1 ml) was added to initiate the Reformatsky reaction then a mixture of S—N—BOC—cyclohexylalanal (18 g), ethyl bromodifluoroacetate (13.6 ml) and THF (100 ml) was added over seven minutes. The reaction was refluxed for minutes further, cooled to 25° C. and partitioned between ethyl acetate (400 ml) and 1M KHSO$_4$ (100 ml). The organic layer was washed with water and saturated aqueous NaCl. It was then dried over MgSO$_4$ and chromatographed on silica gel (pet. ether - ethyl acetate 85:15) to give the desired product as an oil. Addition of hexane caused precipitation of the major diastereomer, S,R—BOC—DFCYS—OEt (4.6 g), as a white solid. This material was dissolved in THF (30 ml), treated with 1.1 eq. 1 N NaOH, and stirred at 25° C. for four hours. Acidification with citric acid and extraction into ethyl acetate afforded S,R—BOC—DFCYS (4.8 g) upon drying (MgSO$_4$) and evaporation. MS (FAB) 52 (m+1).

BOC—LYS(Z)—STA—NHCH$_2$CH(CH$_3$)CH$_2$CH$_3$

BOC—LYS(Z) (1.98 g), STA—NHCH$_2$CH(CH$_3$)CH$_2$CH$_3$ (1.3 g), HOBT.H$_2$O (0.72 g), were mixed together in DMF (15 ml) and cooled to 0° C. DCC (1.1 g) was added, and the mixture was allowed to warm slowly to 25° C. and then stir for 72 hours. The mixture was filtered, and the filtrate was extracted with EtOAc and water. The organic phase was washed with water, sodium bicarbonate solution, and brine. The organic phase was dried over sodium sulfate, filtered, and evaporated. The residue was eluted from silica gel with 1:1 EtOAc/hexane to give 2.7 g of product.

The following compounds are prepared in an analogous manner:

BOC—LYS(Z)—CYSTA—NHCH$_2$CH(CH$_3$)CH$_2$CH$_3$,

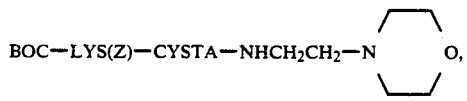

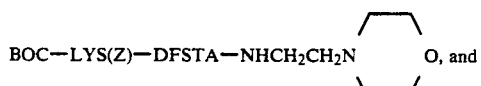

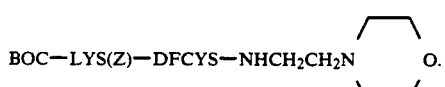

BOC—LYS(CNHCH$_3$)—STA—NHCH$_2$CH(CH$_3$)CH$_2$CH$_3$
‖
S

A solution of BOC—LYS(Z)—STA—NHCH$_2$CH(CH$_3$)CH$_2$CH$_3$ (5.1 g) in MeOH (100 ml) was treated with 20% Pd/C (1.0 g) under Hz atmosphere (50 psi) for six hours at 25° C. Catalyst was removed by filtration and the filtrate was evaporated to a solid. This solid was dissolved in a mixture of CHCl$_3$ (40 ml) and THF (80 ml) and treated with methyl isothiocyanate (0.62 g). The resulting solution was stirred at 25° C. overnight and evaporated. The major product was isolated by flash chromatography on silica gel, eluting with CHCl$_3$—MeOH (98:2) to afford the desired product (4.1 g). MS (FAB) 546 (m+1).

The following compounds were prepared in an analogous manner:

BOC—LYS(CNHMe)—CYSTA—NHCH$_2$CH(CH$_3$)CH$_2$CH$_3$, and
‖
S

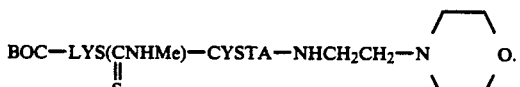

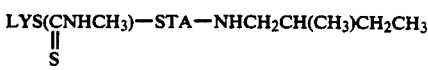

A solution of the above BOC-protected dipeptide (2 g) in CH$_2$Cl$_2$ (40 ml) was treated with methanolic HCl (20 ml), stirring at 25° C. for one hour. The reaction mixture was evaporated and the residue was partitioned between CH$_2$Cl$_2$ (50 ml) and 10% aqueous Na$_2$CO$_3$ (25 ml). The organic layer was dried over MgSO$_4$ and evaporated to a gum. TLC R$_f$=0.1 (silica gel, CHCl$_3$—MeOH, 9:1).

The following compounds are prepared in an analogous manner:

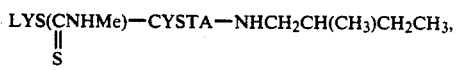

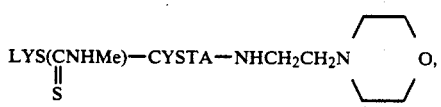

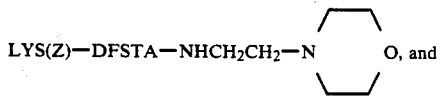

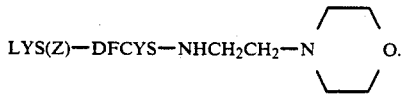

HIS(TR)—STA—NHCH$_2$CH(CH$_3$)CH$_2$CH$_3$

A solution of Z—HIS(TR)—S-TA—NHCH$_2$CH(CH$_3$)CH$_2$CH$_3$ (5.4 g) in MeOH (200 ml) was treated with 20% Pd/C (0.5 g) under H$_2$ atmosphere (50 psi) at 25° C. After five hours the catalyst was removed by filtration and the filtrate was evaporated to give a gum (4.4 g). TLC R$_f$=0.2 (silica gel, CHCl$_3$—MeOH, 9:1).

The following compounds are prepared in an analogous manner:

HIS(TR)—CYSTA—NHCH$_2$CH(CH$_3$)CH$_2$CH$_3$, and

H$_2$NCH(CO$_2$Me)CO$_2$CH$_2$Ph

Methyl, benzyl isonitroso malonate was prepared from methylbenzyl malonate (obtained from Aldrich Chemical Corp.) by the procedure described in *Organic Synthesis,* Col. Vol. V, p. 373. The crude product thus obtained was reduced to the title compound by the procedure described in the *Journal of the American Chemical Society,* Vol. 75, p. 1970, Apr. 20, 1953. Crude product was used without further purification or analyses in the following step.

BOC—NHCH(CO$_2$Me)CO$_2$CH$_2$Ph

H$_2$NCH(CO$_2$Me)CO$_2$CH$_2$Ph (94 g) was dissolved in ethyl ether (750 ml) and cooled to 5° C. Di-t-butyldicarbonate (91.7 g) was added and the mixture was held at 4° C. overnight. The mixture was stripped to an orange oil (135 g). This oil was chromatographed on silica gel, eluting with hexane-ethyl acetate (85:15). The major product was recovered as an oil which solidified upon standing (67 g). MS (FAB) 324(m+1).

BOC—NHCH(CO$_2$Me)CO$_2$H

BOC—NHCH(CO$_2$Me)CO$_2$CH$_2$Ph (16.2 g) was dissolved in MeOH (250 ml), to which was added 20% Pd/C (0.66 g). The suspension was purged with H$_2$ for 1.5 hours, filtered, and stripped at 30° C. in vacuo, giving a syrup (12.5 g) which was kept at 4° C. until use in the following step

BOC—NHCH(CO$_2$Me)CO—S-TA—NHCH$_2$CH(CH$_3$)CH$_2$CH$_3$

BOC—NHCH(CO$_2$Me)CO$_2$H (12.5 g) was dissolved in CH$_2$Cl$_2$ (340 ml) and cooled to −3° C. A solution of HOBT.H$_2$O (7.0 g) in DMF (15 ml) was added, followed by a cold solution of DCC (10.6 g) in CH$_2$Cl$_2$ (50 ml). A cold solution of STA—NHCH$_2$CH(CH$_3$)CH$_2$CH$_3$(11.3 g) in CH$_2$Cl$_2$ (60 ml) was then added and the mixture was stored at 4° C. overnight. The mixture was filtered and he filtrate was washed consecutively with 1N citric acid, brine, saturated aqueous NaHCO$_3$, and brine. The organic phase was dried over MgSO$_4$ and stripped to a glass (23.3 g). Chromatography on silica gel, eluting with CHCl$_3$—MeOH (98:2) gives the purified product as a foam (13 9 g). MS (FAB) 460(m+1).

The following compounds were prepared in an analogous manner:

BOC—NHCH(CO$_2$Me)CO—CYSTA—NHCH$_2$CH(CH$_3$)CH$_2$CH$_3$,

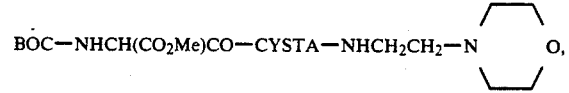

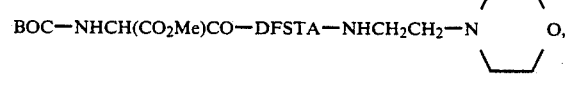

BOC—NHCH(CO$_2$Me)CO—DFCYS—NHCH$_2$CH(CH$_3$)CH$_2$CH$_3$,

BOC—NHCH(CO$_2$Me)CO—DFCYS—NHCH$_2$CH$_2$N(CH$_2$CH$_2$OH)$_2$, and

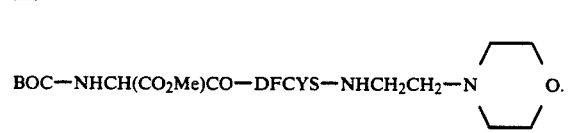

H$_2$NCH(CO$_2$Me)CO—S-TA—NHCH$_2$CH(CH$_3$)CH$_2$CH$_3$

BOC—NHCH(CO$_2$Me)CO—S-TA—NHCH$_2$CH(CH$_3$)CH$_2$CH$_3$ (16.6 g) was dissolved in CH$_2$Cl$_2$ (300 ml), to which was added trifluoroacetic acid (50 ml). After stirring two hours, the mixture was stripped to a syrup which was taken up in ethyl ether-ethyl acetate (1:1). This solution was charged with saturated aqueous NaHCO$_3$ (50 ml), followed by agitation. Additional solid NaHCO$_3$ was added until the mixture became saturated. The organic phase was washed with brine, dried over MgSO$_4$ and stripped to a yellow foam (10.5 g) which was suitable for use in subsequent steps (Example 8) without further purification. MS (FAB) 360 (m+1).

The following compounds are prepared in an analogous manner:

H2NCH(CO2Me)CO—CYSTA—NHCH2CH(CH3)CH2CH3,

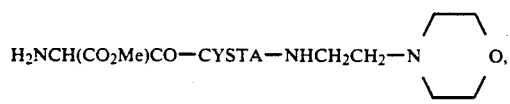

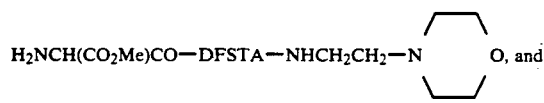

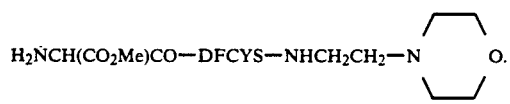

BOC—ALG—STA—NHCH2CH(CH3)CH2CH3

A mixture of BOC—ALG (1.76 g), HOBT.H2O (1.16 g) and DMF (20 ml) was stirred in an ice bath and treated with STA—NHCH2CH(CH3)CH2CH3 (2.0 G) and DCC (1.79 g). The mixture was stirred in an ice bath for three hours and then overnight at room temperature. After filtering, the filtrate was concentrated under high vacuum. The residue was taken up in EtOAc and washed with 1N citric acid, brine, saturated NaHCO3, and brine. After drying over Na2SO4, the solution was concentrated to yield an orange solid which was purified by flash chromatography (MeOH/CHCl3 2:98) to yield BOC—ALG—STA—NHCH2CH(CH3)CH2CH3 (2.1 g) as a white foam MS (FAB) 442(m+1)

The following compounds were obtained in an analogous manner:

BOC—ALG—CYSTA—NHCH2CH(CH3)CH2CH3,

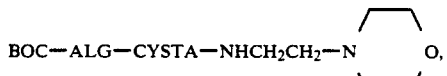

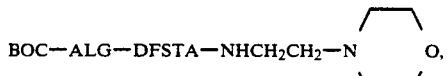

BOC—ALG—DFCYS—NHCH2CH(CH3)CH2CH3, and
BOC—ALG—DFCYS—NHCH2CH2N(CH2CH2OH)2.

We claim:
1. A peptide of the formula

A—X—Y—W—U                                    I or a pharmaceutically acceptable salt thereof wherein

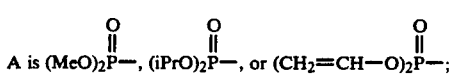

X is PHE or TYR(OMe);
Y is HIS, TZA, MET, PGY, PPG, ALG, ATM, or GLY;
W is STA, CYSTA, CAD, DFCYS, DFKCYS, DFSTA, or DFKSTA;
U is hydrogen,

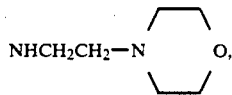

NHCH2CH2N(CH2CH2OH)2,                            or
NHCH2CH(CH3)CH2CH3.

2. A peptide according to claim 1 and being

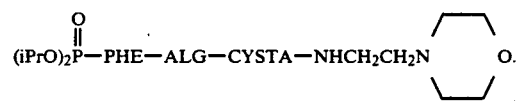

3. A peptide according to claim 1 and being

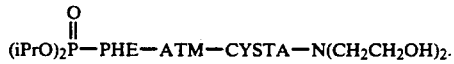

4. A peptide according to claim 1 and being

5. A peptide according to claim 1 and being

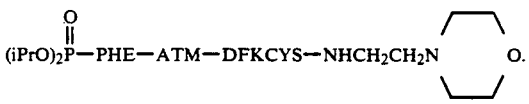

6. A peptide according to claim 1 and being

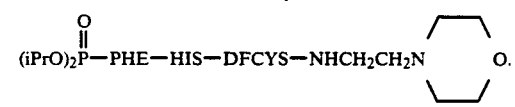

7. A peptide according to claim 1 and being

8. A peptide according to claim 1 and being

9. A compound according to claim 1 and being

10. A peptide according to claim 1 and being

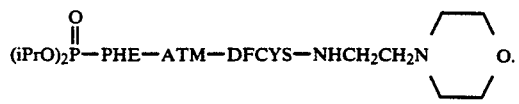

11. A pharmaceutical composition comprising a renin-inhibitory effective amount of a peptide as claimed in claim 1 together with a pharmaceutically acceptable carrier.

12. A method of treating renin-associated hypertension which comprises administering to a mammal a pharmaceutical composition as claimed in claim 11.

13. A pharmaceutical composition comprising a renin associated hyperaldosteronism-inhibitory effective amount of a peptide as claimed in claim 1 together with a pharmaceutically acceptable carrier.

14. A method of treating renin associated hyperaldosteronism which comprises administering to a mammal a pharmaceutical composition as claimed in claim 13.

15. A pharmaceutical composition comprising an amount effective for treating renin associated congestive heart failure of a peptide as claimed in claim 1 together with a pharmaceutically acceptable carrier.

16. A method of treating renin associated congestive heart failure which comprises administering to a mammal a pharmaceutical composition as claimed in claim 15.

17. A method of determining the presence of renin-associated hypertension in a patient, comprising administering to such a patient, at a hypotensive dosage level and as a single dose, a peptide according to claim 1, followed by monitoring of said patient's blood pressure.

* * * * *